(12) United States Patent
Gracias et al.

(10) Patent No.: US 11,331,085 B2
(45) Date of Patent: May 17, 2022

(54) BIORESORBABLE SELF-FOLDING TOOLS FOR SURGERY, SINGLE CELL CAPTURE AND MANIPULATION

(71) Applicant: THE JOHNS HOPKINS UNIVERSITY, Baltimore, MD (US)

(72) Inventors: David Gracias, Baltimore, MD (US); Kate Malachowski, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 484 days.

(21) Appl. No.: 14/885,598

(22) Filed: Oct. 16, 2015

(65) Prior Publication Data
US 2016/0106399 A1    Apr. 21, 2016

Related U.S. Application Data

(60) Provisional application No. 62/064,795, filed on Oct. 16, 2014.

(51) Int. Cl.
| A61B 10/02 | (2006.01) |
| A61B 10/04 | (2006.01) |
| A61B 10/06 | (2006.01) |

(52) U.S. Cl.
CPC .......... *A61B 10/0233* (2013.01); *A61B 10/04* (2013.01); *A61B 10/06* (2013.01); *A61B 2010/0225* (2013.01)

(58) Field of Classification Search
CPC ........ A61B 2010/0208; A61B 10/0233; A61B 10/04; A61B 2010/0225; A61B 10/06
See application file for complete search history.

(56) References Cited

U.S. PATENT DOCUMENTS

2010/0326071 A1*  12/2010  Gracias ................. B81B 3/0024
                                                    60/527

FOREIGN PATENT DOCUMENTS

| WO | WO 2008108862 A2 * | 9/2008 | ........... A61K 9/0024 |
| WO | 2008108862 A2 | 11/2008 | |
| WO | 2009111737 A1 | 11/2009 | |
| WO | 2010129319 A2 | 11/2010 | |
| WO | 2011139796 A2 | 11/2011 | |
| WO | 2011163618 A2 | 12/2011 | |
| WO | 2012061138 A2 | 5/2012 | |

(Continued)

OTHER PUBLICATIONS

Hwang et al (2012) A physically transient form of silicon electronics. Science. Sep. 28, 2012;337(6102):1640-4.

(Continued)

*Primary Examiner* — Patrick Fernandes
(74) *Attorney, Agent, or Firm* — Casimir Jones, S.C.; Jeffrey W. Childers

(57) ABSTRACT

Microgrippers adapted to capture, manipulate, and contain single cells in both in vitro and in vivo cell applications are disclosed. The energy required to actuate these microgrippers is derived from the release of residual stress and does not require any wires, tethers, or batteries. Because the microgrippers are made from biocompatible and biosorbable materials, they do not accumulate in tissue. Accordingly, they can be used for in vivo applications, such as for gripping single cells in tissue biopsies.

25 Claims, 22 Drawing Sheets

(56) References Cited

FOREIGN PATENT DOCUMENTS

WO  WO 2012154511 A2 * 11/2012 ............. A61B 10/02

OTHER PUBLICATIONS

Desmarais et al (2012) Microfabricated devices for biomolecule encapsulation. Electrophoresis. Sep. 2012;33(17):2639-49. doi: 10.1002/elps.201200189.

Pandey et al (2011) Algorithmic design of self-folding polyhedra. Proc Natl Acad Sci U S A. Dec. 13, 2011;108(50):19885-90. doi: 10.1073/pnas.1110857108. Epub Dec. 2, 2011.

Leong et al (2009) Tetherless thermobiochemically actuated microgrippers. Proc Natl Acad Sci U S A. Jan. 20, 2009;106(3):703-8. doi: 10.1073/pnas.0807698106. Epub Jan. 12, 2009.

Leong et al (2008) Thin film stress driven self-folding of microstructured containers. Small. Oct. 2008;4(10):1605-9. doi: 10.1002/smll.200800280.

Solovev et al (2009) Catalytic microtubular jet engines self-propelled by accumulated gas bubbles. Small. Jul. 2009;5(14):1688-92. doi: 10.1002/smll.200900021.

Altschuler et al (2010) Cellular heterogeneity: do differences make a difference? Cell. May 14, 2010;141(4):559-63. doi: 10.1016/j.cell.2010.04.033.

Arora et al (2006) Membrane folding to achieve three-dimensional nanostructures: Nanopatterned silicon nitride folded with stressed chromium hinges. Appl Phys Lett 88:053108.

Ashkin et al (1986) Observation of a single-beam gradient force optical trap for dielectric particles . Optics Letters 11:288-290.

Azioune et al (2009) Simple and rapid process for single cell micro-patterning. Lab Chip. Jun. 7, 2009;9(11):1640-2. doi: 10.1039/b821581m. Epub Mar. 10, 2009.

Bassik et al (2008) Patterning Thin Film Mechanical Properties to Drive Assembly of Complex 3D Structures. Advanced Materials 20(24):4760-4764.

Bassik et al (2009) Microassembly based on hands free origami with bidirectional curvature. Applied Physics Letters 95:091901.

Bassik et al (2010) Enzymatically triggered actuation of miniaturized tools. J Am Chem Soc. Nov. 24, 2010;132(46):16314-7. doi: 10.1021/ja106218s. Epub Sep. 17, 2010.

Beckman et al (2012) Impact of genetic dynamics and single-cell heterogeneity on development of nonstandard personalized medicine strategies for cancer. Proc Natl Acad Sci U S A. Sep. 4, 2012;109(36):14586-91. doi: 10.1073/pnas.1203559109. Epub Aug. 13, 2012.

Berns et al (1998) Laser scissors and tweezers. Methods Cell Biol. 1998;55:71-98.

Calbo et al (2011) A functional role for tumor cell heterogeneity in a mouse model of small cell lung cancer. Cancer Cell. Feb. 15, 2011;19(2):244-56. doi: 10.1016/j.ccr.2010.12.021.

Chalapat et al (2013) Self-organized origami structures via ion-induced plastic strain. Adv Mater. Jan. 4, 2013;25(1):91-5. doi: 10.1002/adma.201202549. Epub Oct. 1, 2012.

Charnley et al (2009) Integration column: microwell arrays for mammalian cell culture. Integr Biol (Camb). Dec. 2009;1(11-12):625-34. doi: 10.1039/b918172p. Epub Oct. 14, 2009.

Chronis et al (2005) Electrothermally Activated SU-9 Microgripper for Single Cell Manipulation in Solution. Journal of Microelectromechanical Systems 14(4):857-863.

Chua et al (2003) Out-of-plane high-Q inductors on low-resistance silicon. Journal of Microelectromechanical Systems 12(6):989-995.

Dicarlo et al (2006) Single-cell enzyme concentrations, kinetics, and inhibition analysis using high-density hydrodynamic cell isolation arrays. Anal Chem. Jul. 15, 2006;78(14):4925-30.

Dicarlo et al (2012) Introduction: why analyze single cells? Methods Mol Biol. 2012;853:1-10. doi: 10.1007/978-1-61779-567-1_1.

Dicarlo et al (2006) Dynamic single cell culture array. Lab Chip. Nov. 2006;6(11):1445-9. Epub Sep. 4, 2006.

Ding et al (2012) On-chip manipulation of single microparticles, cells, and organisms using surface acoustic waves. Proc Natl Acad Sci U S A. Jul. 10, 2012;109(28):11105-9. doi: 10.1073/pnas.1209288109. Epub Jun. 25, 2012.

Fang et al (2010) Evolution of stress in evaporated silicon dioxide thin films. Chinese Optics Letters 8(1):119-122.

Fernandes et al (2009) Toward a miniaturized mechanical surgeon. Materials Today 12(10):14-20.

Friede et al (1996) Some comments on so-called 'silicon monoxide'. Journal of Non-Crystalline Solids 204(2):202-203.

Gautrot et al (2010) Exploiting the superior protein resistance of polymer brushes to control single cell adhesion and polarisation at the micron scale. Biomaterials. Jun. 2010;31(18):5030-41. doi: 10.1016/j.biomaterials.2010.02.066. Epub Mar. 26, 2010.

Gultepe et al (2012) Biopsy with thermally-responsive untethered microtools. Adv Mater. Jan. 25, 2013;25(4):514-9. doi: 10.1002/adma.201203348. Epub Oct. 9, 2012.

Gultepe et al (2013) Biologic tissue sampling with untethered microgrippers. Gastroenterology. Apr. 2013;144 (4):691-3. doi: 10.1053/j.gastro.2013.01.066. Epub Feb. 8, 2013.

Halg et al (1990) On a nonvolatile memory cell based on micro-electro-mechanics . Micro Electro Mechanical Systems, 1990. Proceedings, An Investigation of Micro Structures, Sensors, Actuators, Machines and Robots. IEEE.

Harazim et al (2012) Fabrication and applications of large arrays of multifunctional rolled-up SiO/SiO2 microtubes. J. Mater. Chem., 2012,22, 2878-2884.

Hill et al (1967) Stress in films of silicon monoxide. British Journal of Applied Physics, vol. 18, No. 1 p. 13.

Huang et al (2005) Nanomechanical Architecture of Strained Bilayer Thin Films: From Design Principles to Experimental Fabrication. Adv Mater vol. 17, Issue 23 Dec. 2005 pp. 2860-2864.

Huang et al (2009) Rolled-up transparent microtubes as two-dimensionally confined culture scaffolds of individual yeast cells. Lab Chip. Jan. 21, 2009;9(2):263-8. doi: 10.1039/b810419k. Epub Oct. 23, 2008.

Iler et al (1973) Effect of adsorbed alumina on the solubility of amorphous silica in water. Journal of Colloid and Interface Science 43(2):399-108.

Kane et al (1999) Patterning proteins and cells using soft lithography. Biomaterials. Dec. 1999;20(23-24):2363-76.

Kazuyoshi et al (2003) Self-Assembly of Microstage Using Micro-Origami Technique on GaAs. Japanese Journal of Applied Physics 42:4079-4083.

Kim et al (1996) Influence of substrates on the elastic reaction of films for the microindentation tests. Thin Solid Films vol. 283, Issues 1-2, Sep. 1, 1996, pp. 12-16.

Kim et al (2013) Fabrication and characterization of magnetic microrobots for three-dimensional cell culture and targeted transportation. Adv Mater. Nov. 6, 2013;25(41):5863-8. doi: 10.1002/adma.201301484. Epub Jul. 17, 2013.

Leclair et al (2011) Surface patterning using plasma-deposited fluorocarbon thin films for single-cell positioning and neural circuit arrangement. Biomaterials. Feb. 2011;32(5):1351-60. doi: 10.1016/j.biomaterials.2010.10.051. Epub Nov. 13, 2010.

Leplan et al (1996) Kinetics of residual stress evolution in evaporated silicon dioxide films exposed to room air. J. Appl. Phys. 79, 6926.

Lindstrom et al (2010) Overview of single-cell analyses: microdevices and applications. Lab Chip. Dec. 21, 2010;10(24):3363-72. doi: 10.1039/c0lc00150c. Epub Oct. 22, 2010.

Lindstrom et al (2011) Miniaturization of biological assays—overview on microwell devices for single-cell analyses. Biochim Biophys Acta. Mar. 2011;1810(3):308-16. doi: 10.1016/j.bbagen.2010.04.009. Epub May 6, 2010.

Lucio et al (2003) Measurements and modeling of water transport and osmoregulation in a single kidney cell using optical tweezers and videomicroscopy. Phys Rev E Stat Nonlin Soft Matter Phys. Oct. 2003;68(4 Pt 1):041906. Epub Oct. 10, 2003.

Ma et al (2011) A clinical microchip for evaluation of single immune cells reveals high functional heterogeneity in phenotypically similar T cells. Nat Med. Jun. 2011;17(6):738-43. doi: 10.1038/nm.2375. Epub May 22, 2011.

(56) References Cited

OTHER PUBLICATIONS

Mandal et al (2012) Thermoresponsive micropatterned substrates for single cell studies. PLoS One. 2012;7(5): e37548. doi: 10.1371/journal.pone.0037548. Epub May 31, 2012.
Mannello et al (2013) Understanding breast cancer stem cell heterogeneity: time to move on to a new research paradigm. BMC Med. Jul. 23, 2013;11:169. doi: 10.1186/1741-7015-11-169.
Mei et al (2008) Versatile Approach for Integrative and Functionalized Tubes by Strain Engineering of Nanomembranes on Polymers. Adv Mater 20(21):4085-4090.
Mei et al (2009) Fabrication, self-assembly, and properties of ultrathin AlN/GaN porous crystalline nanomembranes: tubes, spirals, and curved sheets. ACS Nano. Jul. 28, 2009;3(7):1663-8. Epub Jun. 24, 2009.
Moiseeva et al (2007) Single-mask microfabrication of three-dimensional objects from strained bimorphs. • Journal of Micromechanics and Microengineering, vol. 17, No. 9 p. N63.
Navin et al (2010) Inferring tumor progression from genomic heterogeneity. Genome Res. Jan. 2010;20(1):68-80. doi: 10.1101/gr.099622.109. Epub Nov. 10, 2009.
Nikishkov et al (2003) Curvature estimation for multilayer hinged structures with initial strains. J. Appl. Phys. 94, 5333 (2003); http://dx.doi.org/10.1063/1.1610777.
Nilsson et al (2009) Review of cell and particle trapping in microfluidic systems. Anal Chim Acta. Sep. 7, 2009;649(2):141-57. doi: 10.1016/j.aca.2009.07.017. Epub Jul. 14, 2009.
Park et al (2011) Continuous dielectrophoretic bacterial separation and concentration from physiological media of high conductivity. Lab Chip. Sep. 7, 2011;11(17):2893-900. doi: 10.1039/c1lc20307j. Epub Jul. 21, 2011.
Peng et al (2004) A three-dimensional flow control concept for single-cell experiments on a microchip. 1. Cell selection, cell retention, cell culture, cell balancing, and cell scanning. Anal Chem. Sep. 15, 2004;76(18):5273-81.
Peng et al (2004) A three-dimensional flow control concept for single-cell experiments on a microchip. 2. Fluorescein diacetate metabolism and calcium mobilization in a single yeast cell as stimulated by glucose and pH changes. Anal Chem. Sep. 15, 2004;76(18):5282-92.
Pietras et al (2011) Cancer stem cells in tumor heterogeneity. Adv Cancer Res. 2011;112:255-81. doi: 10.1016/B978-0-12-387688-1.00009-0.
Prinz et al (2000) Free-standing and overgrown InGaAs/GaAs nanotubes, nanohelices and their arrays. Physica E: Low-dimensional Systems and Nanostructures vol. 6, Issues 1-4, Feb. 2000, pp. 828-831.
Prinz et al (2003) Three-Dimensional Self-Shaping Nanostructures Based on Free Stressed Heterofilms. Russian Physics Journal Jun. 2003, vol. 46, Issue 6, pp. 568-576.
Rimstidt et al (1980) The kinetics of silica-water reactions. Geochimica et Cosmochimica Acta vol. 44, Issue 11, Nov. 1980, pp. 1683-1699.
Roman et al (2007) Single-cell manipulation and analysis using microfluidic devices. Anal Bioanal Chem. Jan. 2007;387(1):9-12.
Sakar et al (2010) Single cell manipulation using ferromagnetic composite microtransporters. Appl. Phys. Lett. 96, 043705 (2010); http://dx.doi.org/10.1063/1.3293457.
Sasaki et al (2004) Three-dimensional SOI-MEMS constructed by buckled bridges and vertical comb drive actuator. Selected Topics in Quantum Electronics, IEEE Journal of (vol. 10 , Issue: 3 ) 455-461.
Schmidt et al (2001) Nanotechnology. Thin solid films roll up into nanotubes. Nature. Mar. 8, 2001;410(6825):168.
Schulmeister et al (2003) TEM investigation on the structure of amorphous silicon monoxide. Journal of Non-Crystalline Solids vol. 320, Issues 1-3, Jun. 1, 2003, pp. 143-150.
Shenoy et al (2012) Self-folding thin-film materials: From nanopolyhedra to graphene origami. MRS Bulletin / vol. 37 / Issue 09 / Sep. 2012, pp. 847-854.
Smith et al (2012) Lab-in-a-tube: ultracompact components for on-chip capture and detection of individual micro-/nanoorganisms. Lab Chip. May 8, 2012;12(11):1917-31. doi: 10.1039/c2lc21175k. Epub Mar. 22, 2012.
Soler et al (2013) Self-propelled micromotors for cleaning polluted water. ACS Nano. Nov. 26, 2013;7(11):9611-20. doi: 10.1021/nn405075d. Epub Nov. 7, 2013.
Stellman et al (2007) Dynamics of Nanostructured Origami. Microelectromechanical Systems, Journal of (vol. 16 , Issue: 4 ) 932-949.
Townes-Anderson et al (1998) Micromanipulation of retinal neurons by optical tweezers. Mol Vis. Jul. 30, 1998;4:12.
Valero et al (2005) Apoptotic cell death dynamics of HL60 cells studied using a microfluidic cell trap device. Lab Chip. Jan. 2005;5(1):49-55. Epub Dec. 6, 2004.
Wheeler et al (2003) Microfluidic device for single-cell analysis. Anal Chem. Jul. 15, 2003;75(14):3581-6.
Xi et al (2012) Rolled-up magnetic microdrillers: towards remotely controlled minimally invasive surgery. Nanoscale. Feb. 21, 2013;5(4):1294-7. doi: 10.1039/c2nr32798h.
Xie et al (2002) Near-infrared Raman spectroscopy of single optically trapped biological cells. Opt Lett. Feb. 15, 2002;27(4):249-51.
Zhang et al (2008) Optical tweezers for single cells. J R Soc Interface. Jul. 6, 2008;5(24):671-90. doi: 10.1098/rsif.2008.0052.
Zhang et al (2004) Free-standing Si/SiGe micro- and nano-objects. Physica E: Low-dimensional Systems and Nanostructures vol. 23, Issues 3-4, Jul. 2004, pp. 280-284.

\* cited by examiner

BIORESORBABLE SELF-FOLDING TOOLS FOR SURGERY, SINGLE CELL CAPTURE AND MANIPULATION

CROSS-REFERENCE TO RELATED APPLICATIONS

This application claims the benefit of U.S. Provisional Application No. 62/064,795, filed Oct. 16, 2014, which is incorporated herein by reference in its entirety.

FEDERALLY SPONSORED RESEARCH OR DEVELOPMENT

This invention was made with government support under OD004346, awarded by the National Institutes of Health. The government has certain rights in the invention.

BACKGROUND

Due to the large size of tools that are typically utilized for surgical diagnostics and biological analyses, cellular samples are often relatively large in size. Consequently, the data collected from tissue biopsied samples and related assays average over a multitude of cells. That average, however, often may not accurately represent the behavior of individual cells, particularly if the cells of interest are a small fraction of the population. Further, it can be challenging to draw conclusions about dynamic or transient behaviors of single cells by looking at large populations (Altschuler et al., 2010; Ma et al., 2011; Di Carlo et al., 2012). For example, tumors have long been known to be heterogeneous populations of cells with varying phenotypes and genotypes, proliferation rate, potential for metastasis, and drug responsiveness, yet how these heterogeneities affect their progression are only beginning to be understood (Navin et al., 2010; Calbo et al., 2011; Pietras, 2011; Mannello, 2013).

Single cell analyses may be necessary to differentiate the behavior of a cell subpopulation from the bulk measurement, particularly in the fields of cancer biology, genomics, proteomics, stem cell biology, and hematology (Di Carlo et al., 2012). Given the heterogeneous nature of cultures, tumors, and tissues, the ability to capture, contain and analyze single cells also is important for diagnostics, therapeutics and surgery. This aspect is especially important as treatments for cancer, immune diseases, and tissue regeneration move toward personalized medicine (Beckman et al., 2012).

SUMMARY

In one aspect, the presently disclosed subject matter provides a device for sampling one or more single cells in a tissue sample or biological fluid, the device comprising a pre-stressed bilayer in operational communication with one or more rigid segments, wherein the one or more rigid segments comprise a plurality of arms having sharp or tapered tips, wherein the device has a first configuration capable of being actuated to at least a second configuration in response to one or more stimuli, and wherein the device is adapted to capture, manipulate, or encapsulate a single cell from the tissue sample or biological fluid when in the at least second configuration.

In another aspect, the presently disclosed subject matter provides a method for fabricating a device for sampling one or more single cells in a tissue sample or biological fluid, the method comprising: (a) depositing a sacrificial layer on a substrate; (b) patterning a pre-stressed bilayer on the sacrificial layer, wherein the pre-stressed bilayer has a predetermined shape; (c) patterning one or more rigid segments; (d) optionally molding a stimuli-responsive polymer over the pre-stressed bilayer and one or more rigid segments; and (e) optionally releasing the device from the substrate to provide an untethered device for sampling one or more single cells in a tissue sample or biological fluid.

In yet other aspects, the presently disclosed subject matter provides a method for sampling a single cell in a tissue sample or biological fluid of a subject, the method comprising: (a) introducing to the subject a plurality of sampling devices comprising: a pre-stressed bilayer in operational communication with one or more rigid segments, wherein the one or more rigid segments comprise a plurality of arms having sharp or tapered tips, wherein the device has a first configuration capable of being actuated to at least a second configuration in response to one or more stimuli, and wherein the device is adapted to capture, manipulate, or encapsulate a single cell from the tissue sample or biological fluid when in the at least second configuration; (b) contacting the plurality of sampling devices with a tissue site or biological fluid; (c) altering a configuration of the plurality of sampling devices from a first configuration to a second configuration while in contact with the tissue or biological fluid, the second configuration adapted such that the sampling device grasps the tissue or samples the biological fluid at a discrete location; and (d) releasing and/or collecting the plurality of sampling devices.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
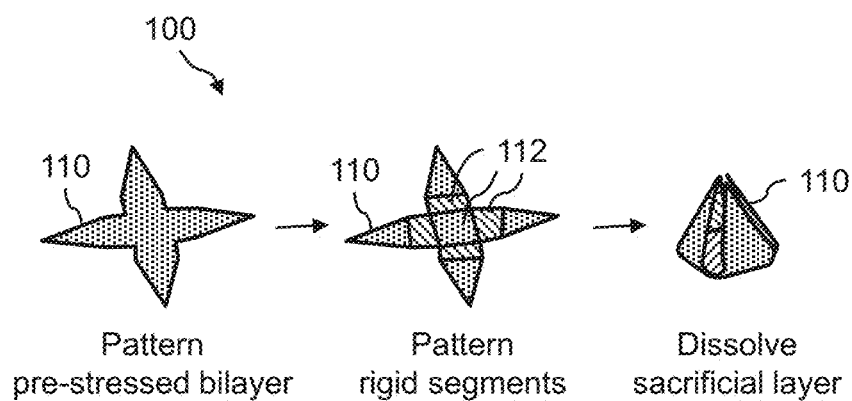
Figure 1B:
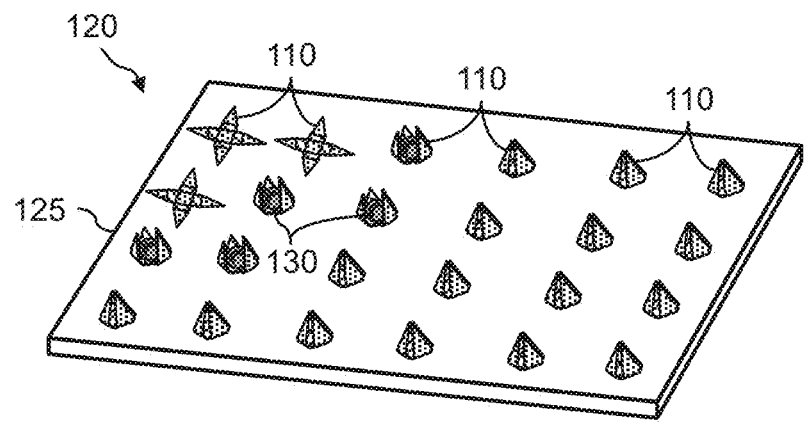
Figure 1C:
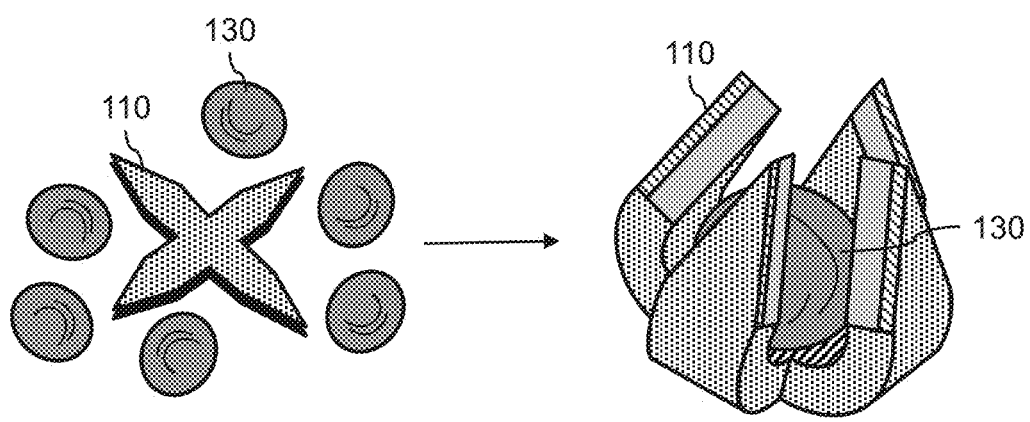
Figure 3A:
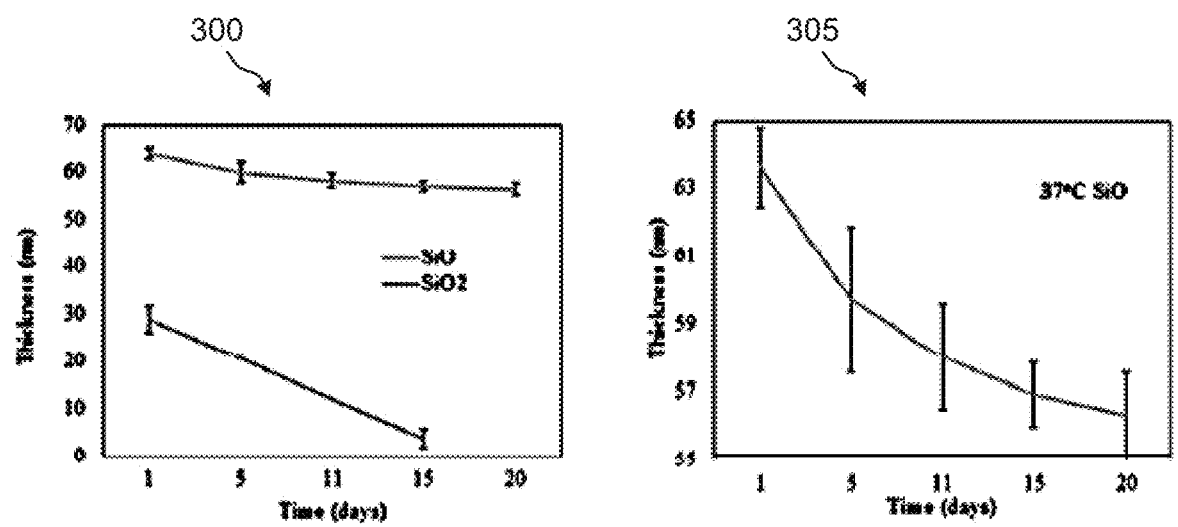
Figure 3B:
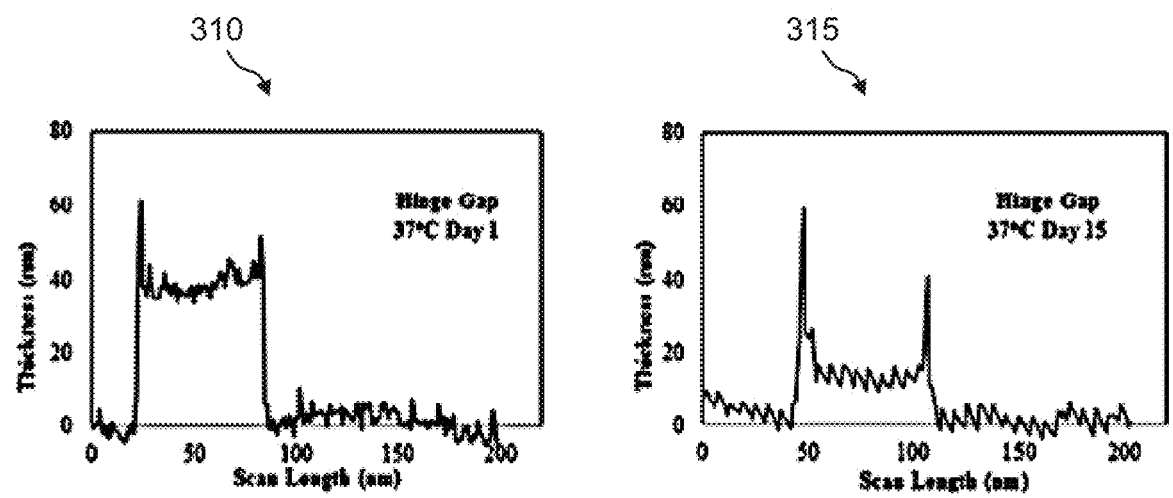
Figure 3C:
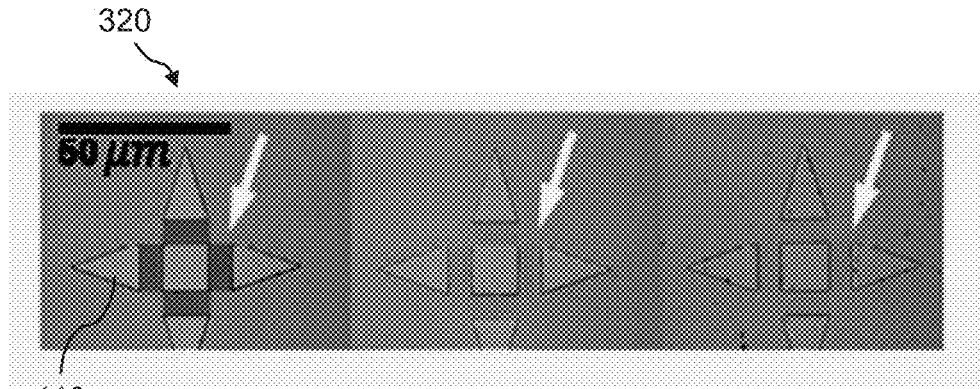
Figure 4A:
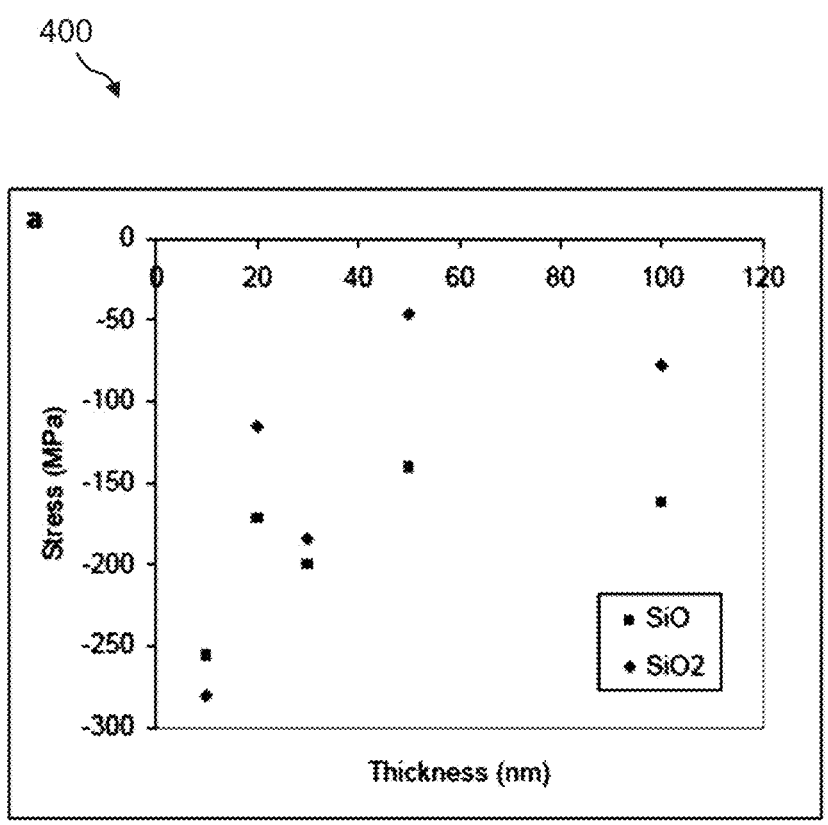
Figure 4B:
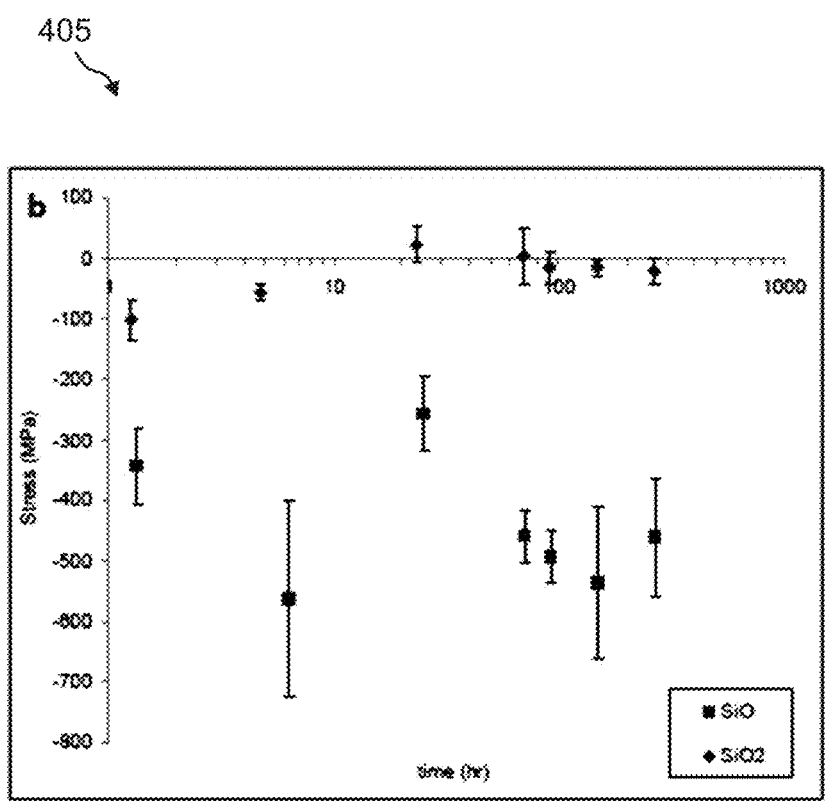
Figure 5A:
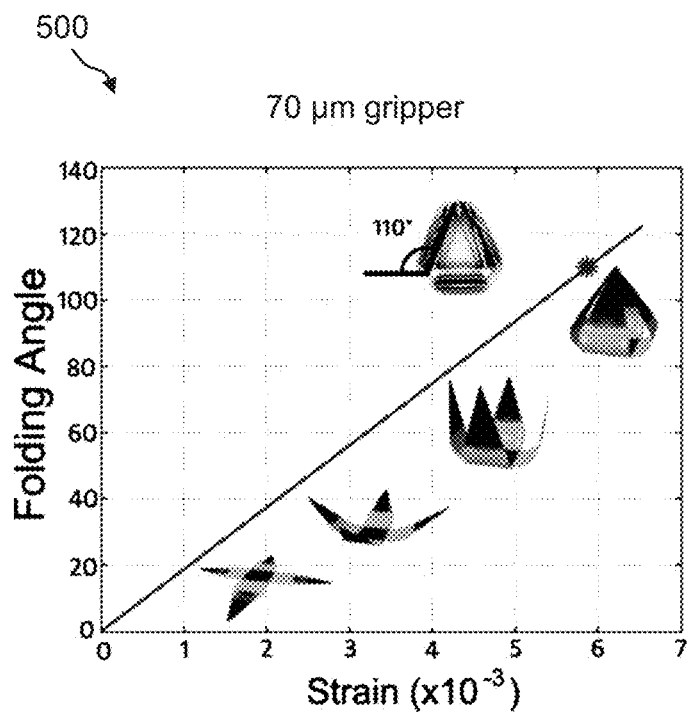
Figure 5A:
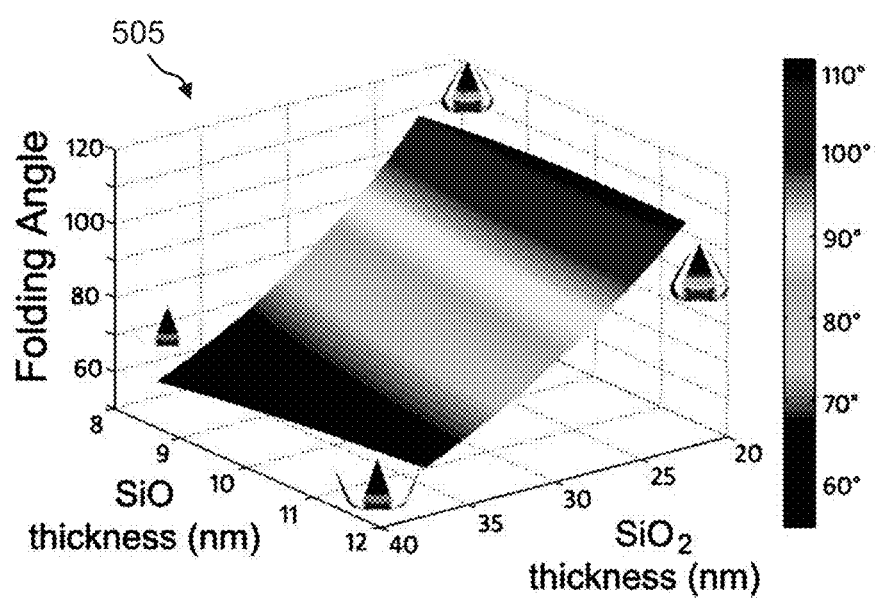
Figure 5B:
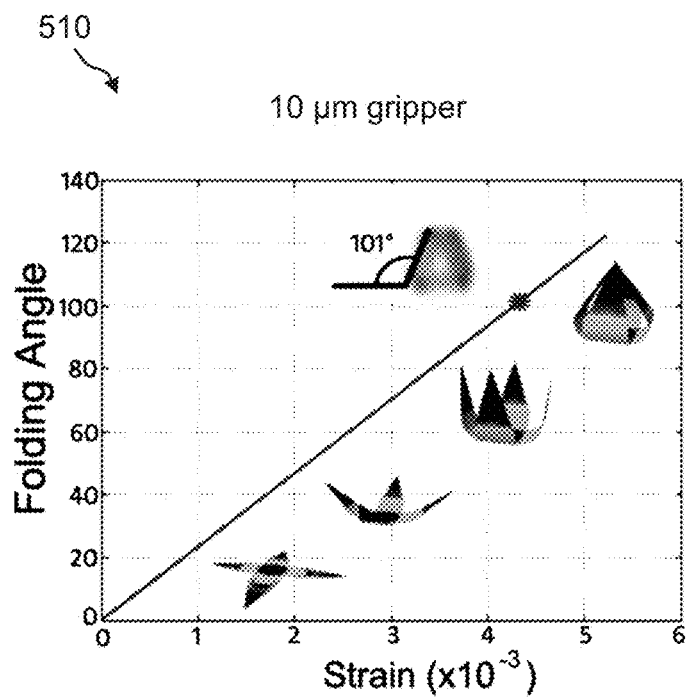
Figure 5B:
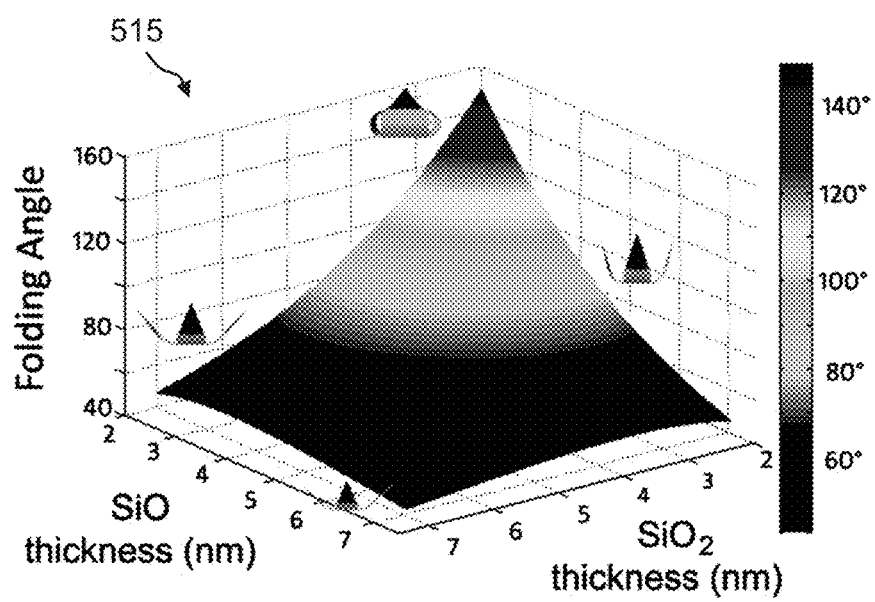
Figure 6A:
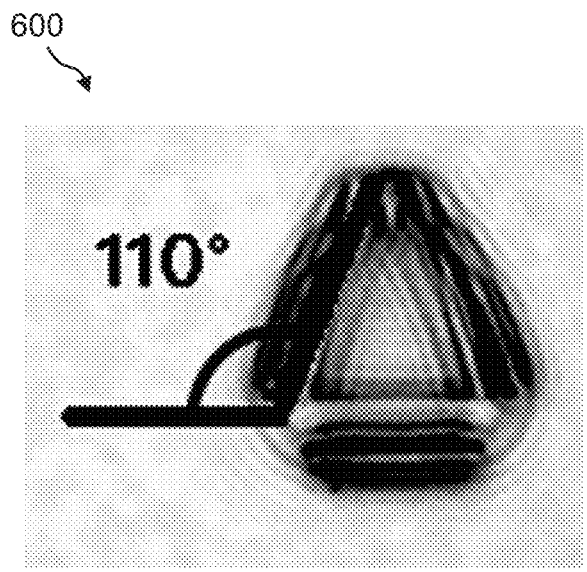
Figure 6B:
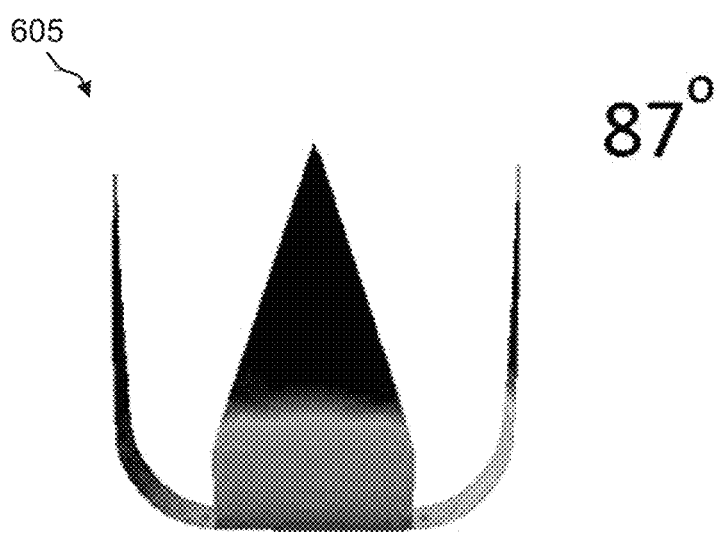
Figure 6C:
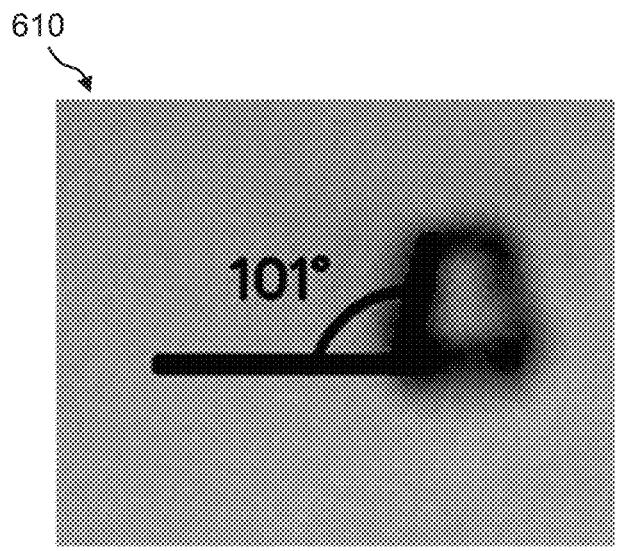
Figure 6D:
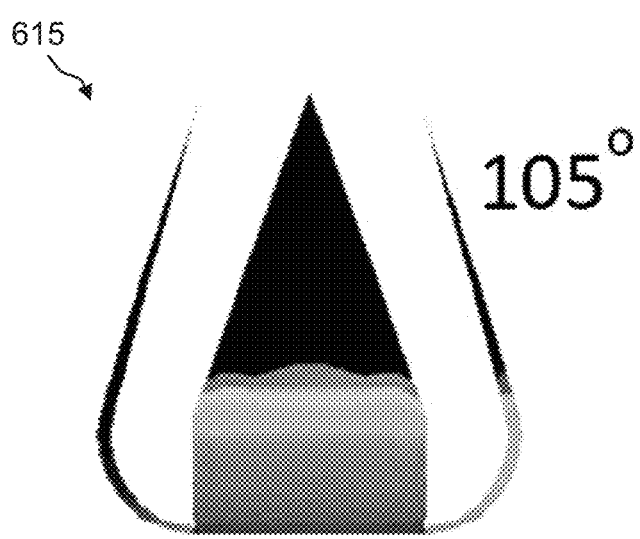
Figure 7A:
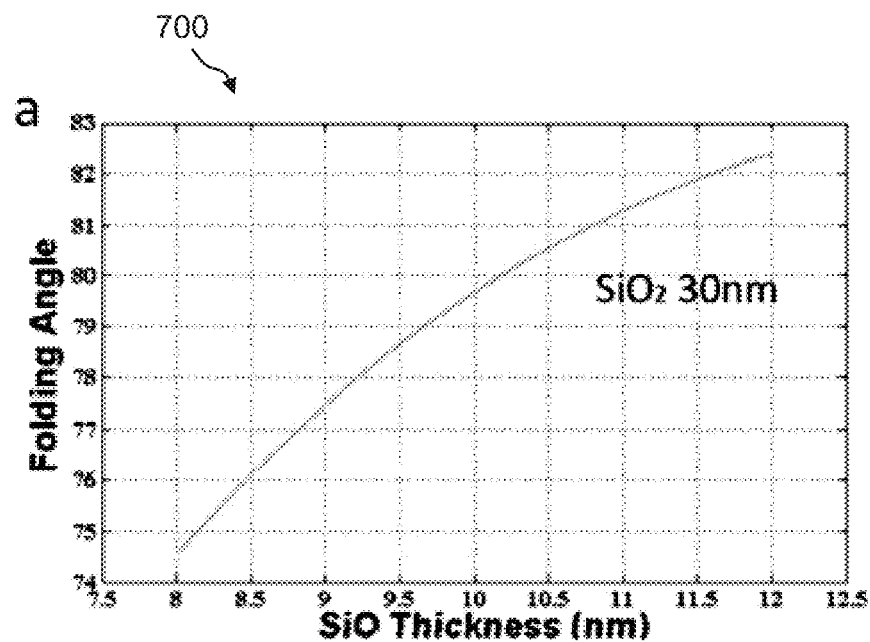
Figure 7B:
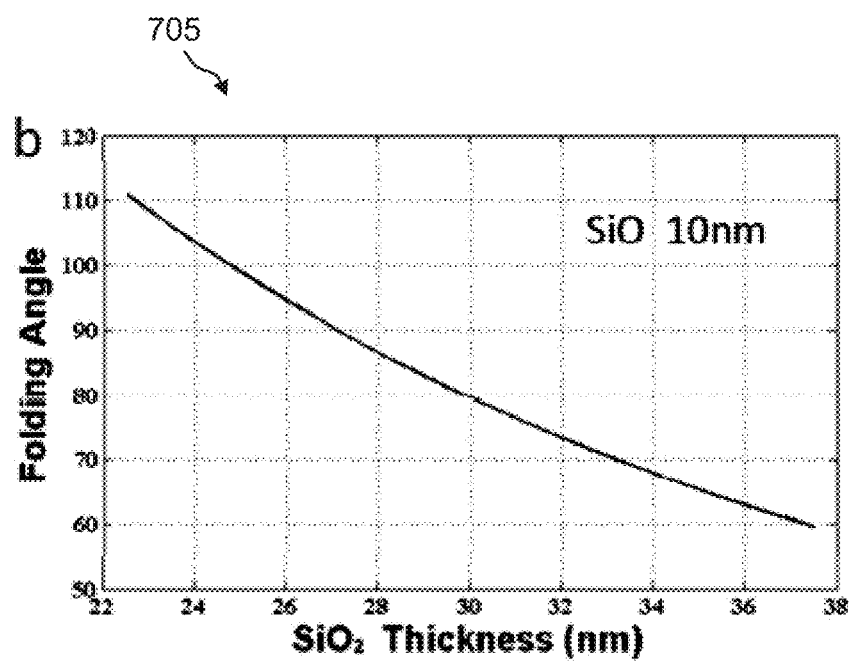
Figure 8A:
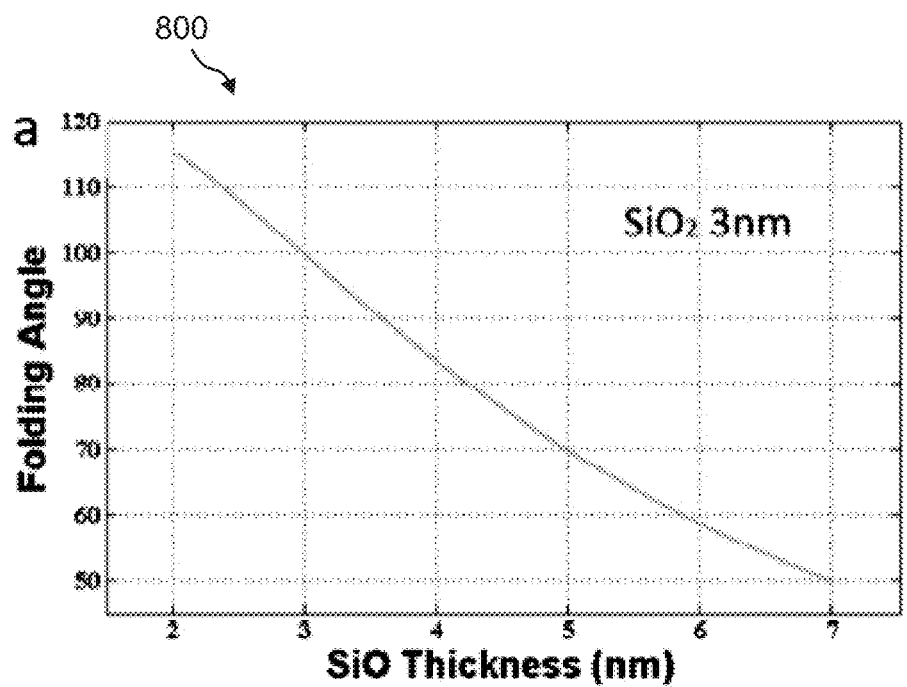
Figure 8B:
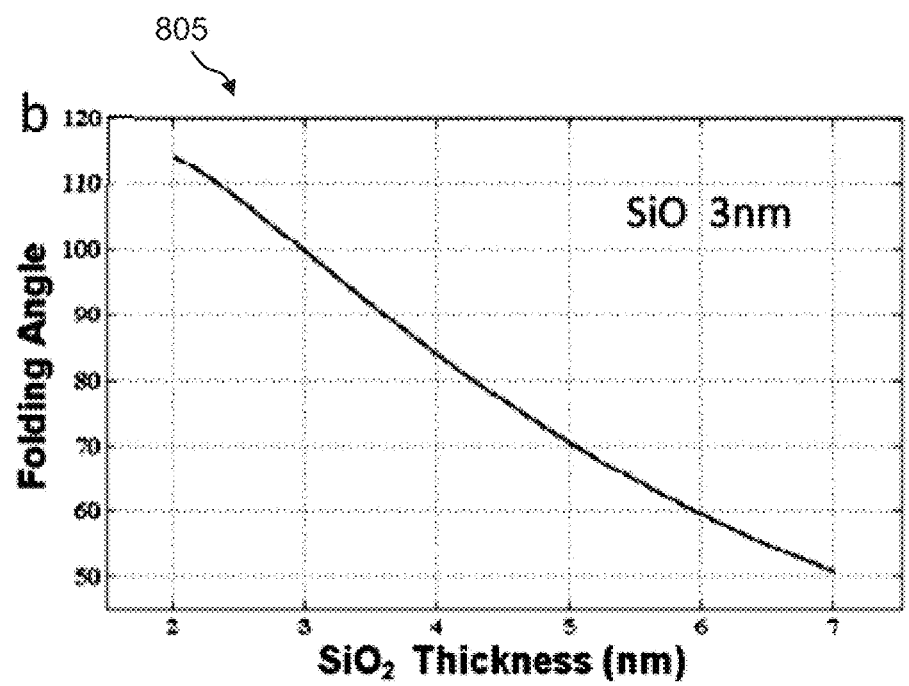
Figure 9A:
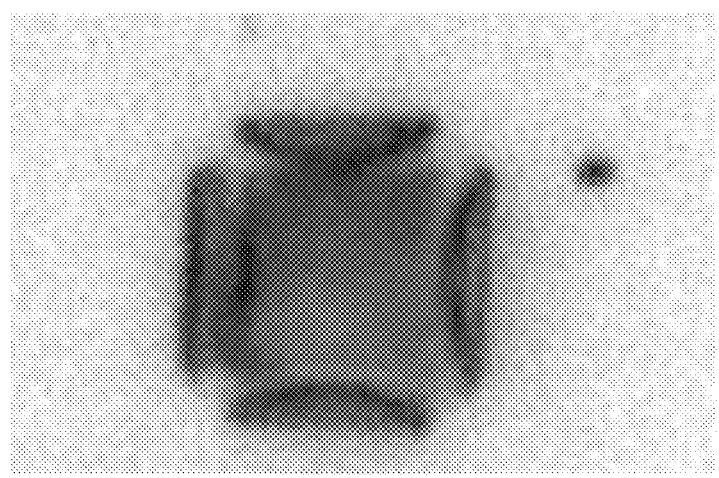
Figure 9B:
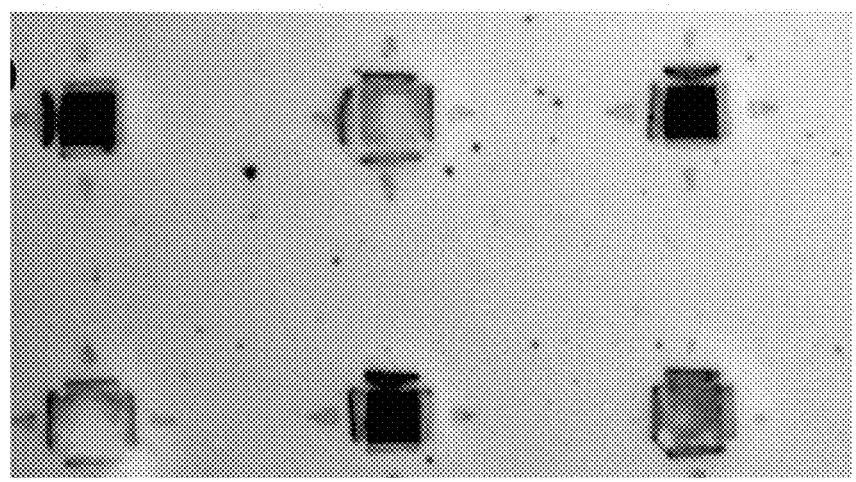
Figure 9C:
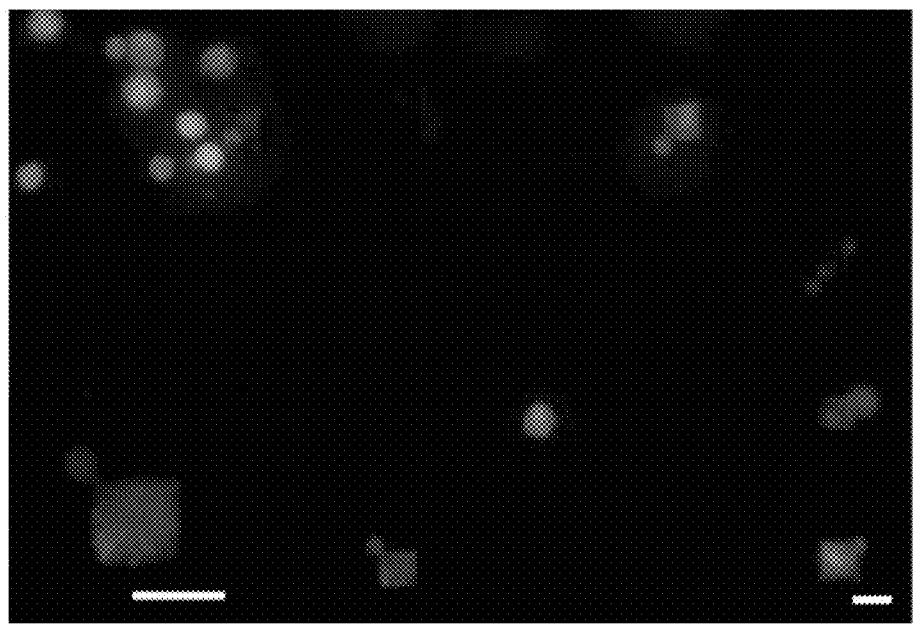
Figure 10A:
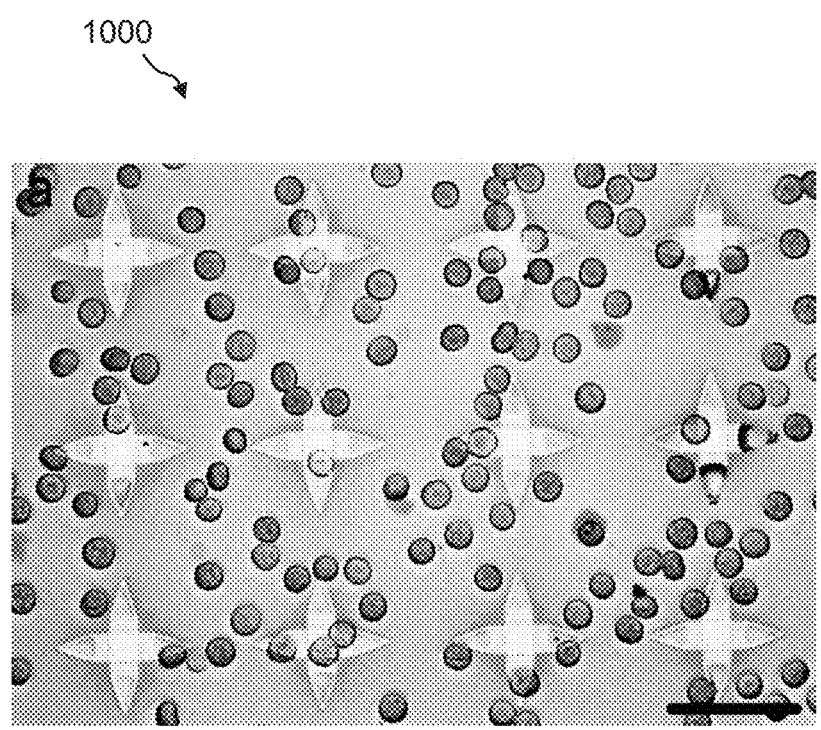
Figure 10B:
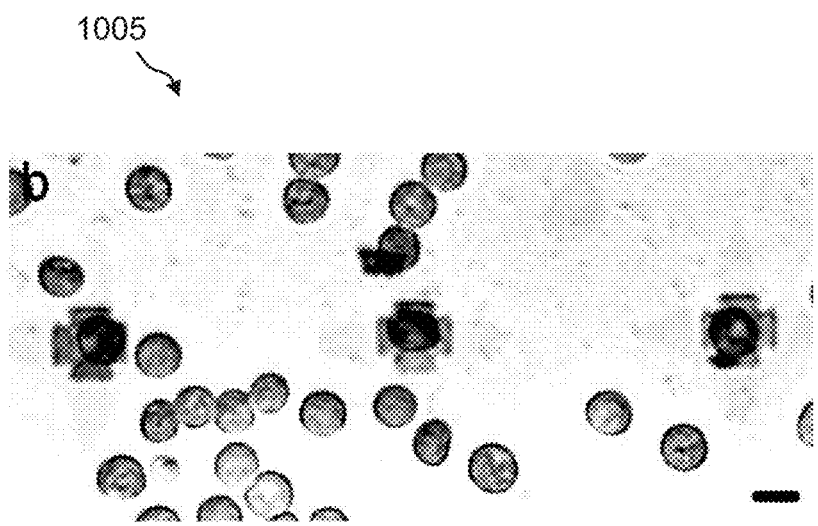
Figure 10C:
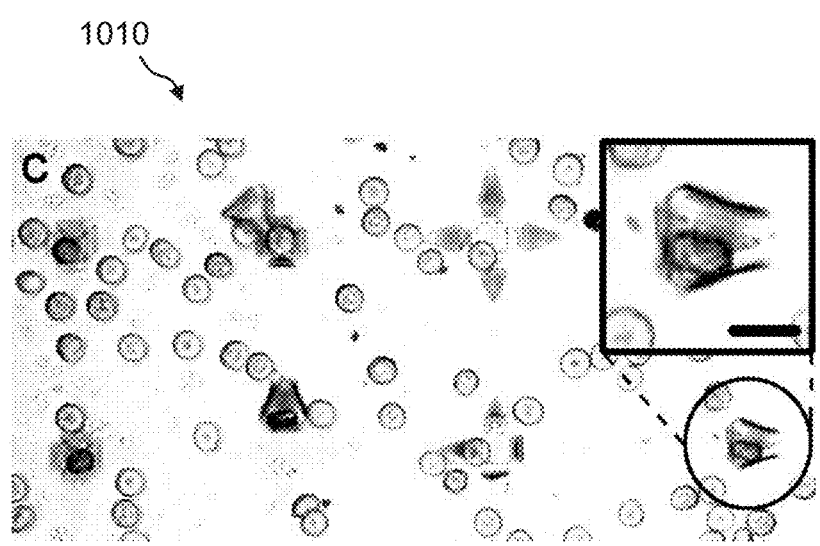
Figure 11A:
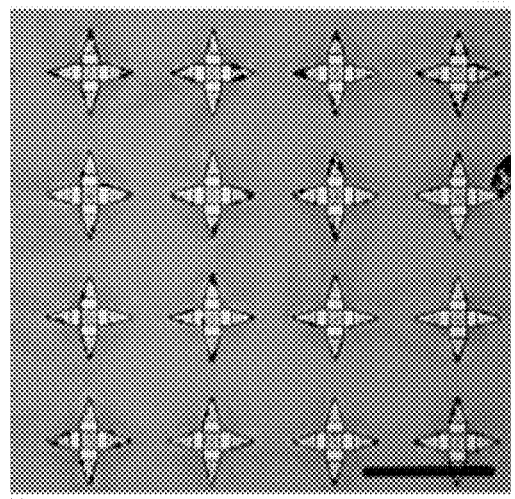
Figure 11B:
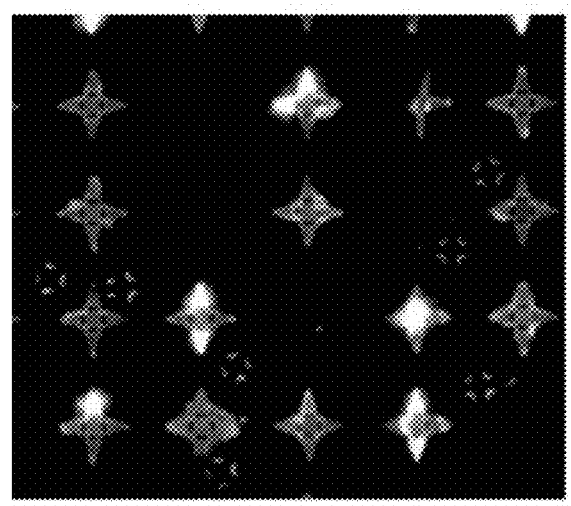
Figure 11C:
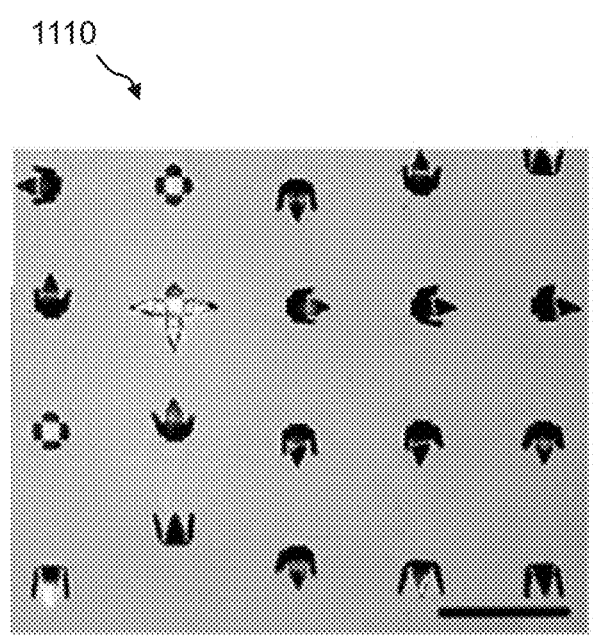

Having thus described the presently disclosed subject matter in general terms, reference will now be made to the accompanying Figures, which are not necessarily drawn to scale, and wherein:

FIG. 1A, FIG. 1B, and FIG. 1C show an illustration of a single cell gripper 110 fabrication process 100 and use on substrates or as free-floating tools: (FIG. 1A) fabrication scheme for creating single cell grippers 110. In this embodiment, the pre-stressed bilayer is a $SiO/SiO_2$ bilayer, while the rigid segments 112 can be made of SiO. Upon dissolution of the sacrificial layer, the arms can be released to close around cells 130. An optional thermo-responsive trigger layer can be molded atop the grippers; (FIG. 1B) illustration of cells 130 captured by single cell microgrippers arrays 120; and (FIG. 1C) illustration of free-floating single cell grippers 110 and red blood cell 130 capture;

FIG. 2A, FIG. 2B, FIG. 2C, FIG. 2D, FIG. 2E, FIG. 2F, and FIG. 2G show optical images of single cell grippers before and after closing: (FIG. 2A) optical image 200 of grippers released from the substrate with open arms prior to closing, in sizes (tip-to-tip) ranging from about 10 µm to about 50 µm; (FIG. 2B and FIG. 2C) zoomed optical images 205 and 210 of 50-µm grippers (FIG. 2B) prior to release from the substrate and (FIG. 2C) closed tightly after release; (FIG. 2D and FIG. 2E) optical images 215 and 220 of 10-µm grippers (FIG. 2D) open and (FIG. 2E) closed. Scale bars are (FIG. 2A, FIG. 2B, and FIG. 2C) 25 µm and (FIG. 2D and FIG. 2E) 10 µm; and (FIG. 2F and FIG. 2G) SEM images 225 and 230 at different magnifications of closed single cell grippers attached to the substrate. Scale bars are (FIG. 2F) 10 µm and (FIG. 2G) 5 µm;

FIG. 3A, FIG. 3B, and FIG. 3C show (FIG. 3A) plot 300 of film thickness versus time quantifying SiO and $SiO_2$ film dissolution and zoomed plot 305 of SiO film dissolution; (FIG. 3B) AFM scans 310 and 315 depicting the dissolution of the gripper hinge from 40 nm thick on Day 1 to approximately 15 nm thick on Day 15; and (FIG. 3C) optical microscopy images 320 of a 70-µm gripper 110 dissolving in PBS at 37° C. The thin hinges dissolve significantly over 15 days, while the thicker SiO rigid segments remain;

FIG. 4A and FIG. 4B show: (FIG. 4A) graph 400 of stress vs. film thickness. SiO and $SiO_2$ are both compressive, but become more tensile with increasing thickness. The variability of the stress is high for both films due to the difficulties associated with measuring wafer bow and stress in such thin films; and (FIG. 4B) graph 405 of stress vs. time. Stress in a 9-nm SiO film remains relatively constant over time, whereas stress in a 27-nm $SiO_2$ film flips to tensile over 1000 hours;

FIG. 5A and FIG. 5B show characterization of thin film stress and gripper folding angle: (FIG. 5A) graphs 500 and 505 depicting the effect of strain and bilayer thickness on folding angle for a 70-µm gripper; and (FIG. 5B) graphs 510 and 515 depicting the effect of strain and bilayer thickness on folding angle for a 10-µm gripper. The inset images of a folded gripper with angle measurement in the left panels are optical microscopy images of actual folded grippers for comparison to the modeled gripper folding. Stars indicate the observed folding angle for each gripper size;

FIG. 6A, FIG. 6B, FIG. 6C, and FIG. 6D show (FIG. 6A and FIG. 6B) experimentally observed 600 (FIG. 6A) and finite element simulated 605 (FIG. 6B) folding of a 70-µm gripper; and (FIG. 6C and FIG. 6D) experimentally observed 610 (FIG. 6C) and finite element simulated 615 (FIG. 6D) folding of a 10-µm gripper. In the model, mismatch strain is calculated as 0.0043 using equations from Example 5 (Boundary Condition) (and data from Table 2 and Table 3;

FIG. 7A and FIG. 7B shows 700 folding angle changes with SiO thickness when $SiO_2$ is fixed as 30 nm (FIG. 7A); and folding angle changes with $SiO_2$ thickness when SiO is fixed as 10 nm (FIG. 7B). In both cases mismatch strain is 0.0043 in 70-µm gripper;

FIG. 8A and FIG. 8B show 800 folding angle change with SiO thickness when $SiO_2$ is fixed as 3 nm (FIG. 8A); and folding angle change with $SiO_2$ thickness when SiO is fixed as 3 nm (FIG. 8B). In both cases mismatch strain is 0.0043 for a 10-µm gripper;

FIG. 9A, FIG. 9B, FIG. 9C, and FIG. 9D show: (FIG. 9A, FIG. 9B, and FIG. 9C) single cell microgripper arrays 900, 905, and 910, respectively. Individual cells captured within the arms of grippers (FIG. 9C, inset). The cell inside the gripper has conformed to the square shape of the gripper base; and (FIG. 9D) SEM image 915 of a cell trapped within the arms of a gripper, with several untrapped cells surrounding. Scale bars are 10 µm;

FIG. 10A, FIG. 10B, and FIG. 10C show capture of single red blood cells and free-floating single cell grippers. Optical images 1000, 1005, and 1010, respectively, of red blood cells trapped in 35-µm $SiO/SiO_2$ grippers: (FIG. 10A) grippers with red blood cells prior to folding and release from the substrate. Scale bar is 35 µm; and (FIG. 10B and FIG. 10C) red blood cells captured by grippers. Scale bars are 10 µm;

FIG. 11A, FIG. 11B, and FIG. 11C show optical images 1100, 1105, and 1110, respectively, of magnetic nickel single cell grippers: (FIG. 11A) Ni/Ni grippers prior to release from the substrate; (FIG. 11B) unfolded Ni/Ni single cell grippers released from the wafer substrate with polymer hinge triggers; and (FIG. 11C) folded Ni/Ni single cell grippers with a folding angle of approximately 85°. Scale bars are 100 µm; and FIG. 12A, FIG. 12B, FIG. 12C, and FIG. 12D show: (FIG. 12A) optical images 1200 and 1205 of microgrippers prior to and (FIG. 12B) after release; (FIG. 12C) schematic 1210 of cell capture with micropatterned topography and biochemicals on gold; and (FIG. 12D) an optical image 1215 showing isolation of single cells within microgrippers. Scale bars are 10 µm.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Bioresorbable Self-Folding Tools for Surgery, Single Cell Capture and Manipulation A wide range of techniques are available for in vitro single cell analysis, and each has advantages and disadvantages in terms of efficiency, cell manipulation, imaging capability, sensitivity, and ability to mimic or actually perform in vivo (Lindstrom and Andersson-Svahn, 2010; Lindstrom and Andersson-Svahn, 2012). These methods include flow cytometry (Lindstrom and Andersson-Svahn, 2010), optical traps (Ashkin et al., 1986; Townes-Anderson et al., 1998; Berns et al., 1998; Xie et al., 2002; Lúicio et al., 2003; Zhang and Liu, 2008), microfluidic traps and devices (Ma et al., 2011; Wheeler et al., 2003; Peng and Li, 2004, 76:5273-5281; Peng and Li, 2004, 76:5282-5292; Valero et al., 2005; Di Carlo, Wu et al., 2006; Di Carlo, Aghdam et al., 2006; Roman et al., 2007; Nilsson et al., 2009; Park et al., 2011; Ding et al., 2012), microwells (Charnley et al., 2009; Lindstrom and Andersson-Svahn, 2011), microtubes (Smith et al., 2012), and 2D surface patterns (Kane et al., 1999; Azioune et al., 2010; Gautrot et al., 2010; Leclair et al., 2011; Mandal et al., 2012). Several miniaturized robotic devices have been created to trap and manipulate particles and cells with precise control (Chronis and Lee, 2005; Sakar et al., 2010; Kim et al., 2013). For example, Chronis et al. demonstrated the manipulation of a 10-µm cell using a wired electrothermally actuated SU-8 gripper (Chronis and Lee, 2005). This device can manipulate cells with high precision, but the electrical wires that control its actuation and its large back-end design limit throughput and in vivo utility. Another SU-8 device, by Sakar et al, provides untethered manipulation of single cells via magnetic forces with minimal fluid disturbance due to its micrometer size and biocompatibility (Sakar et al., 2010). These devices are passive, however, trapping cells in a recess and thus may lose their grip on a cell if they move in the wrong direction or in all three dimensions.

Further, there have been previous studies on the self-curling and roll-up of thin films (Prinz et al., 2000; Schmidt and Eberl, 2001; Kazuyoshi et al., 2003; Chua et al., 2003; Prinz, 2003; Zhanga et al., 2004; Sasaki et al., 2004; Huang et al., 2005; Arora et al., 2006; Moiseeva et al., 2007; Stellman et al., 2007; Bassik et al., 2008; Leong et al., 2008; Mei et al., 2008; Alexander et al., 2009; Leong et al., 2009; Huang et al., 2009; Bassik et al., 2009; Mei et al., 2009; Shenoy and Gracias, 2012; Harzim et al., 2012; Xi et al., 2012; Smith et al., 2012; Soler et al., 2013; Chalapat et al., 2013.

Preferably, an in vitro device would combine the high throughput efficiency of flow cytometry, the incorporation of patterned microfeatures for biomolecular analyses, and the 3D manipulation precision of optical tweezers. Further, it is preferable that the in vivo device be composed of bio-friendly and possibly bioresorbable materials while facilitating tissue excision or targeted capture, robust gripping and retrieval in an autonomous manner (Fernandes and Gracias, 2009).

Accordingly, in some embodiments, the presently disclosed subject matter provides untethered single cell grippers comprise biocompatible materials, including biosorbable, biodegradable, and bioabsorbable materials, such as silicon monoxide and silicon dioxide, for both in vitro and in vivo cell applications. As used herein, the terms bioresorbable, biodegradable, and bioabsorbable can be used interchangeably, and refer to a material that is capable of being dissolved, degraded, or absorbed into a subject's body by natural processes and generally are not harmful to living tissue and do not elicit an undesirable local or systemic effects in the subject. Accordingly, such materials do not require mechanical or manual removal. Suitable materials for use with the presently disclosed subject matter include, but are not limited to, SiO, SiO2, Mg, Zn, Fe, hydrogels, and biosorbable polymers. Biosorbable polymers can include, but are not limited to, poly(glycolic acid) (PGA), poly(L-lactic acid) (PLA), poly(ortho ester) (POE), poly($\varepsilon$-caprolactone) (PCL), and poly(hydroxyl butyrate valerate) (PHBV), and copolymers and blends thereof.

The energy required to actuate these grippers is derived from the release of residual stress and does not require any wires, tethers, or batteries. These microscale grippers, polyhedra, and containers are capable of capturing, manipulating, and containing single cells. Because the tools comprise biosorbable materials, there is no bioaccumulation of the devices within tissue and they can be used for in vivo applications, such as for gripping single cells in tissue biopsies. The presently disclosed tools also are completely tetherless and allow autonomous actuation in response to environmental stimuli. In addition, the presently disclosed tools are small enough to navigate the narrow conduits of the circulatory, respiratory, central nervous, and urinogenital systems, for example.

Patterns can be added on the faces of the grippers to increase cell excision and analyses. Further, microgripper arrays enable surface patterns (including biochemical assays, topography and roughness, or any other surface modification) to be in direct contact with a single cell in all three dimensions. Grippers used in such arrays, in some embodiments, can include one or more unique biomolecular markers, optical patterns, and electronic patterns, and combinations thereof, to enable high-throughput screening of cells.

The presently disclosed grippers are wireless and can be self-actuated by a variety of stimuli, including physical stimuli, such as a change in temperature and/or pH, and/or one or more biological or physiological cues, chemicals, such as acids, and biochemicals, such as enzymes, soluble proteins or surface biomarkers.

As used herein, "biomarker" refers to a characteristic that is an indicator of normal biologic processes, pathogenic processes, or pharmacologic responses to a therapeutic intervention. For example, a biomarker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule. As used herein, a "biochemical" is characterized by being produced by or involving a chemical reaction in a living organism.

The presently disclosed grippers can be actuated spontaneously in response to the specific environmental stimuli or triggered using a heat source, such as a heat pad, infrared, radio-frequency or other electromagnetic field. Such embodiments involve the use of an external trigger/source to actuate the devices once they have reached the desired location. In yet other embodiments, the presently disclosed devices can include nano- or micro-scale additives within the device, such as magnetic nanoparticles to enable imaging, guidance, or remote triggering.

In other embodiments, single cell analyses can occur in a high throughput manner. Examples of products comprising the presently disclosed microgrippers include, but are not limited to, biopsy forceps, clips, clamps, microarray assays, and the like. The presently disclosed tools are alternatively referred to herein as a "microtool," a "tool," a "microgripper," and/or a "gripper."

To prepare the presently disclosed microgrippers, high resolution photolithography can be utilized. High resolution photolithography is a high throughput technique capable of fabricating 500,000 to 10 million single grippers on a 3-inch wafer or more than 100 million on a 12-inch wafer, which is the size of wafers used currently in complementary metal oxide semiconductor (CMOS) fabrication facilities. The presently disclosed tools are mass producible so that millions of tools can be fabricated and actuated all at once. Additionally, they can be patterned in all three dimensions and actuated to close around single cells en masse.

The thickness of the films can be varied to control the fold angle and the sharpness of the tips facilitates capture and containment of cells. As compared to previously described stimuli "μ-grippers" that were used to biopsy cell samples and porcine organs under in vitro, ex vivo and in vivo conditions (Leong et al., 2009; Bassik et al., 2010; Gultepe et al., 2012; Gultepe et al., 2013), in some embodiments, the presently disclosed grippers are thirty times smaller, requiring significantly thinner hinges and new materials to achieve a tight radius of curvature.

Since the larger grippers were previously only utilized in the gastrointestinal (GI) tract, it is envisioned that the presently disclosed grippers could be used in tighter spaces, such as within the circulatory, respiratory, urinogenital or central nervous systems; however, there are more stringent requirements on biocompatibility and biodegradability for these applications.

Silicon (Si) and silicon dioxide ($SiO_2$) react with water via hydrolysis to form $Si(OH)_4$ (Rimstidt and Barnes, 1980; Iler, 1973), and thus dissolve into deionized (DI) water and various biofluids (Rimstidt and Barnes, 1980; Hwang et al., 2012) as previously reported by Hwang et al. in their work on dissolvable electronics (Hwang et al., 2012). That study demonstrated that Si dissolution in PBS at 37° C. proceeded at a rate of 4.5 nm/day. Additionally, electronic devices made from Si, $SiO_2$ and other dissolvable materials were implanted sub-dermally into mice with no significant inflammatory reactions. After 3 weeks, only faint residues of the electronics remained.

Silicon monoxide (SiO) is a two-phase, non-homogenous mixture of amorphous Si and $SiO_2$ and has been previously paired with $SiO_2$ to form tightly rolled tubes with microscale radii of curvature when e-beam evaporated in nanometer thicknesses (Smith et al., 2012; Mei et al., 2008; Shenoy and Gracias, 2012; Harazim et al., 2012). Thus, these two materials were selected for the presently disclosed single cell grippers for their biocompatibility, biosorption, and self-curling properties.

A. Microgripper Devices

In some embodiments, the presently disclosed grippers comprise a pre-stressed bilayer optionally comprising a layer, e.g., a stimuli-responsive polymer, which can trigger a change in configuration or conformation. One of ordinary skill in the art would recognize that any stimuli-responsive polymer is suitable for use in the presently disclosed devices as a triggering mechanism for actuating the device to fold from one configuration or conformation to another. As referred to herein, a stimuli-responsive polymer, also referred to as "smart" polymers or "environmentally sensitive" polymers, can undergo a change in their microstructure, for example, from a hydrophilic to a hydrophobic state, triggered by changes in the environment. External stimuli, including, but not limited to, a change in temperature, a change in pH, ionic strength, magnetic and electric fields, light, ultrasound, and chemical species, can trigger changes in the environment. The macroscopic changes that occur in the micro structure generally are reversible. Therefore, the polymer is capable of returning to its initial state when the stimulus is removed. Classes of stimuli-responsive polymers can be characterized by their physical forms; (a) linear free chains in solution, (b) covalently cross-linked reversible and physical gels, and (c) chain adsorbed or surface-grafted forms.

Temperature and pH sensitivity are common properties utilized in stimuli-responsive polymers because: some disease states manifest themselves by a change in temperature and/or pH; and the response to the stimulus, e.g., temperature and/or pH, can be tuned to a desired temperature and/or pH range. The most extensively investigated temperature/pH sensitive systems are based on poly(N-isopropylacrylamide) (PNIPAM). PNIPAM can be chain-end functionalized with carboxylic acid, NHS ester, amine, and maleimide groups to develop a series of temperature- and pH-sensitive polymers. Further, NIPAM can be copolymerized with methacrylic acid to impart pH sensitivity. Also pH and temperature sensitive hydrogels can be prepared using NIPAM, acrylic acid and a di-acrylamide crosslinker. For example, PNIPAM exhibits a LCST of about 32° C. in aqueous solution, and the lower critical solubility temperature (LCST) can be easily manipulated by copolymerization of NIPAM with suitable monomers. In particular embodiments, the stimuli-responsive material ispolymer.

The presently disclosed grippers preferably are bio-inert, and also may be wholly or partially bioresorbable. For example, the grippers may be composed completely of bio-inert materials or may be coated with a bio-inert material. A number of bio-inert materials useful as coatings are well known in the art. In some embodiments, the grippers comprise an inert metal (such as gold), a polymer (such as polyimide, polyether ether ketone (PEEK), polytetrafluoroethylene, polyvinylidene fluoride, N-isopropylacrylamide (NIPAM), poly(propylene fumarate) (PPF) and polyamide), or a combination thereof.

Certain polymeric materials also are biocompatible and bioresorbable. Therefore, in some embodiments, the grippers are biodegradable.

As described hereinabove, the energy required for actuating the gripping action is intrinsically provided to the grippers as a consequence of residual stress stored in the pre-stressed bilayer. As a result, the grippers require no wires, tethers or batteries to effectuate gripping.

Different sizes and/or shapes of grippers can be provided depending on the specific application and site within a subject where they will be deployed. Due to their small millimeter or sub-millimeter size, a large number, e.g., hundreds, thousands, or more of the grippers can be dispersed in a small amount of liquid and moved by fluid flow.

Accordingly, in some embodiments, the presently disclosed subject matter provides a device for sampling one or more single cells in a tissue sample or biological fluid, the device comprising a pre-stressed bilayer in operational communication with one or more rigid segments, wherein the one or more rigid segments comprise a plurality of arms having sharp or tapered tips, wherein the device has a first configuration capable of being actuated to at least a second configuration in response to one or more stimuli, and wherein the device is adapted to capture, manipulate, or encapsulate a single cell from the tissue sample or biological fluid when in the at least second configuration.

In some embodiments, the pre-stressed bilayer comprises $SiO/SiO_2$ and the one or more rigid segments comprise SiO. In other embodiments, the pre-stressed bilayer comprises Ni/Ni and the one or more rigid segments comprise Ni.

In particular embodiments, the device has a shape selected from the group consisting of a star and a sphere, wherein each shape comprises the plurality of arms having sharp or tapered tips.

In some embodiments, the plurality of arms further comprises one or more materials that either attract or repel the cell and combinations thereof. In particular embodiments, the one or more materials are selected from the group consisting of gold and fibronectin.

In yet other embodiments, the plurality of arms are patterned with one or more features selected from the group consisting of one or more holes and one or more raised topographical structures.

In particular embodiments, the device has a dimension having a range from about 10 μm to about 70 μm measured from at least one tip of the plurality of arms to at least one other tip of the plurality of arms.

In certain embodiments, the device is optically transparent.

In some embodiments, the device comprises one or more openings or slits at an intersection of at least two arms, wherein the one or more openings or slits are in fluid communication with the single cell captured by the device such that nutrients, waste, and physiological biochemical can flow to and from the cell.

In particular embodiments, the device is adapted to be deployed in a subject. In yet more particular embodiments, the device is adapted to be deployed in a subject by a method or device selected form the group consisting of a capsule, a sustained-release capsule, an endoscope, a laparoscope, a suppository, an enema, and an injection.

In yet other embodiments, the presently disclosed subject matter provides an array comprising a plurality of gripper devices. Grippers used in such arrays, in some embodiments, can include unique biomolecular markers, optical patterns, and/or electronic patterns to enable high-throughput screening of cells.

B. Fabrication of Microgripper Devices

One of ordinary skill in the art would recognize that any known process can be used to fabricate the presently disclosed devices. For example, the presently disclosed devices can be fabricated by molding, three-dimensional printing, a layer-by-layer process, spin-coating photolithography, and the like.

Accordingly, in some embodiments, the presently disclosed subject matter provides a method for fabricating a device for sampling one or more single cells in a tissue sample or biological fluid, the method comprising: (a) depositing a sacrificial layer on a substrate; (b) patterning a pre-stressed bilayer on the sacrificial layer, wherein the pre-stressed bilayer has a predetermined shape; (c) patterning one or more rigid segments; (d) optionally molding a stimuli-responsive polymer over the pre-stressed bilayer and one or more rigid segments; and (e) optionally releasing the device from the substrate to provide an untethered device for sampling one or more single cells in a tissue sample or biological fluid.

In some embodiments, the sacrificial layer comprises copper (Cu). In some embodiments, the substrate comprises a silicon (Si) wafer.

In particular embodiments, the pre-stressed bilayer comprises $SiO/SiO_2$ and the one or more rigid segments comprise SiO. In other embodiments, the pre-stressed bilayer comprises Ni/Ni and the one or more rigid segments comprise Ni.

In certain embodiments, each layer of the pre-stressed bilayer has a thickness having a range from about 2 nm to about 30 nm. In particular embodiments, each layer of the pre-stressed bilayer has a thickness selected from the group consisting of 3 nm SiO/3 nm $SiO_2$, 8 nm SiO/15 nm $SiO_2$, 9 nm SiO/27 nm $SiO_2$, and 10 nm SiO/30 nm $SiO_2$.

In some embodiments, the device has a dimension having a range from about 10 μm to about 70 μm measured from at least one tip of the plurality of arms to at least one other tip of the plurality of arms. In certain embodiments, the device has a folding angle ranging from about 90° to about 115°.

In particular embodiments, the stimuli-responsive polymer comprises paraffin.

In other embodiments, the method further comprises selectively patterning or depositing on one or more of the plurality of arms one or more materials that either attract or repel the cell and combinations thereof. In certain embodiments, the one or more materials are selected from the group consisting of gold and fibronectin.

In yet other embodiments, the method further comprises patterning the plurality of arms with one or more features selected from the group consisting of one or more holes and one or more raised topographical structures.

In embodiments for fabricating an array of gripper devices, the method further comprises depositing a center portion of the pre-stressed bilayer directly on the substrate to form an array of devices on the substrate.

C. Methods of Sampling Using Microgripper Devices

The presently disclosed grippers can be designed to target and ultimately attach to a desired area or location in a subject's body that is afflicted with a disease, condition, disorder, or a symptom thereof. The presently disclosed grippers can be used to sample a tissue site or to perform micro surgery at a site. Further, the presently disclosed grippers can be deployed in a subject's body in numbers sufficient to improve the statistical likelihood of delivery to a targeted or desired area for sampling thereof. Further, any number of grippers may be deployed within a body cavity. In various embodiments, 1 to 10, 1 to 50, 1 to 100, 1 to 250, 1 to 500, 1 to 1000 or more grippers are deployed and may be optionally retrieved from a body cavity.

Because the presently disclosed grippers, in some embodiments, are freestanding and untethered, they can be ingested by the subject, e.g., via a sustained-release capsule, deployed to a diseased site via an invasive scope, such as an endoscope or laparoscope, or otherwise administered to the subject, e.g., via a suppository, enema or injection. After being administered to the subject, the grippers can be activated in response to a physical or biological cue to anchor the gripping element to targeted or desired tissue or biological fluid. In general, such grippers preferably mimic biological appendages, such as claws. The grippers may be any shape that may facilitate grasping of targeted tissue or biological fluid.

As provided hereinabove, the presently disclosed grippers may be made having a dimension ranging from about 5 microns to about 100 microns, including about 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, and 100 μm. In some embodiments, the grippers are small enough to be introduced into a subject in a capsule or pill that can be taken orally. The term "capsule," as used herein, refers to a relatively stable shell, either hard-shelled or soft-shelled, that can be used to enclose a presently disclosed gripper device. The capsule or pill also can be coated to provide for a time release or sustained release of the grippers to a targeted or desired location or area within a subject's body. One of ordinary skill in the art would appreciate that the presently disclosed grippers can be combined with other packaging methods or delivery media for administration to a subject. In other embodiments, the grippers are small enough to be introduced using catheters into a subject, such as in the GI tract. In some embodiments, the number of grippers administered to a subject has a range of anywhere between about two to multiple million devices.

The methodology and device of the presently disclosed subject matter may be used to deliver a gripper device to any area of the body. Generally, grippers are deployed to a body cavity, such as a hollow organ of the body, for example, the gastrointestinal tract. As such, the term "cavity of a subject" is intended to refer to internal surfaces and spaces of the body, as well as external surfaces of the body.

In some embodiments, the tissue site or biological fluid is selected from the group consisting of the esophagus, stomach, duodenum, small intestine, and large intestine, and, in other embodiments, the tissue site is or biological fluid selected from the group consisting of the circulatory, respiratory, urinogenital, and central nervous systems. The tissue site or biological fluid, however, may be any tissue area or biological fluid that is capable of receiving the grippers. Such tissue sites or biological fluid include, diseased tissue, such as tissues selected from the group consisting of a tumor, fistula, and abscess, or diseased biological fluid. In further embodiments, the gripper device may grasp non-diseased cells. The terms "diseased cells" or "diseased site" as used herein refer to any condition, dysfunction or disorder of that tissue or site that damages or interferes with the normal function of a cell, tissue, biological fluid, or organ.

A "tumor," as used herein, refers to all neoplastic cell growth and proliferation, whether malignant or benign, and all precancerous and cancerous cells and tissues. A "fistula," as used herein, refers to an abnormal connection or passageway between two epithelium-lined organs or vessels. An "abscess," as used herein, refers to a collection of pus that has accumulated within a tissue because of an inflammatory process. The terms "non-diseased tissue" or "non-diseased site" are used herein to refer to a tissue or site that has normal function of a cell, tissue, or organ.

When sampling on or near the GI tract is desired, the presently disclosed methods also can be used to determine which tissue site along the GI tract the grippers will grasp. The biological cues may be different for different parts of the GI tract. For example, the pH in the stomach is much more acidic than in the rest of the GI tract, and therefore, pH as a biological cue may be used to actuate the grippers. As another example, a tumor in the GI tract may produce certain biomarkers, such as interleukin, that can be used as a biological cue for actuation of the grippers. As still another example, inflammatory bowel disease also may produce unique biomarkers that can be used to actuate the grippers and only deliver a drug to the affected sites in the GI tract. Also, if the grippers are in a capsule, the capsule may degrade in certain parts of the GI tract depending on its composition, thereby releasing the plurality of grippers at or near those parts of the GI tract that degraded the capsule.

Although a preferred embodiment of the presently disclosed methods is for the grippers to be administered by an oral or rectal route, other methods of administering the presently disclosed gripper devices are envisioned by the disclosure herein. More particularly, the grippers may be administered to a subject by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The term "disease" or "disorder," as used herein, refers to an impairment of health or a condition of abnormal functioning. The term "syndrome," as used herein, refers to a pattern of symptoms indicative of some disease or condition. The term "condition," as used herein, refers to a variety of health states and is meant to include disorders, diseases, or injuries caused by any underlying mechanism or disorder, and includes the promotion of healthy tissues and organs.

Accordingly, in some embodiments, the presently disclosed subject matter provides a method for sampling a single cell in a tissue sample or biological fluid of a subject, the method comprising: (a) introducing to the subject a plurality of sampling devices comprising: a pre-stressed bilayer in operational communication with one or more rigid segments, wherein the one or more rigid segments comprise a plurality of arms having sharp or tapered tips, wherein the device has a first configuration capable of being actuated to at least a second configuration in response to one or more stimuli, and wherein the device is adapted to capture, manipulate, or encapsulate a single cell from the tissue sample or biological fluid when in the at least second configuration; (b) contacting the plurality of sampling devices with a tissue site or biological fluid; (c) altering a configuration of the plurality of sampling devices from a first configuration to a second configuration while in contact with the tissue or biological fluid, the second configuration adapted such that the sampling device grasps the tissue or samples the biological fluid at a discrete location; and (d) releasing and/or collecting the plurality of sampling devices.

In some embodiments, the method further comprises inserting the plurality of sampling devices into a capsule before introducing the plurality of sampling devices to the subject. In particular embodiments, the plurality of sampling devices comprises between about 2 to about 10,000 sampling devices.

In certain embodiments, the one or more stimuli is selected from the group consisting of a change in temperature, a change in pH, an acid, a biochemical, an enzyme, a soluble protein, and a surface biomarker. In particular embodiments, the change in temperature comprises changing the temperature above about body temperature. In yet more particular embodiments, the change in temperature comprises changing the temperature above about 32° C.

In some embodiments, the tissue site or biological fluid is selected from the group consisting of the esophagus, stomach, duodenum, small intestine, large intestine, the circulatory system, the respiratory system, the urinogenital system, central nervous system.

In particular embodiments, the tissue site or biological fluid comprises diseased tissue or diseased cells. In yet more particular embodiments, the diseased tissue is selected from the group consisting of a tumor, a fistula, and an abscess.

In certain embodiments, the sampling a single cell in a tissue sample or biological fluid of a subject comprises diagnosing the subject for a disease, condition, disorder, or symptom. In particular embodiments, the disease, condition, disorder, or symptom is a disease, condition, disorder, or symptom of the gastrointestinal (GI) tract, the circulatory system, the respiratory system, the urinogenital system, central nervous system. In yet more particular embodiments, the disease, condition, disorder, or symptom comprises a cancer.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth. The term "plurality" as used herein means "one or more."

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLE

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Materials and Methods

SiO and SiO2 Dissolution Study:
50 nm thick films of SiO and $SiO_2$ were evaporated by e-beam evaporation at rates of 0.1 nm/s and 0.3 nm/s, respectively, on bare Si wafers in the shape of 1000 μm by 1000 μm squares. 70 μm grippers were fabricated with 10 nm SiO and 30 nm $SiO_2$ thick hinges and 150 nm thick SiO rigid segments as described below on bare Si wafers. Both sets of samples were submerged in 50 mL of phosphate buffered saline (PBS, pH 7.4) at 37° C. and the film thicknesses were measured using an Atomic Force Microscope (AFM) and a Filmetrics film thickness measurement tool every other day. The Filmetrics tool was calibrated using a bare Si wafer. Prior to measuring, each sample was removed from PBS, rinsed with DI water, and finally dried with compressed air. Each measurement was an average of nine points per wafer over three wafers. The PBS was replaced over each sample after each measurement. Microgripper fabrication: To fabricate the microgrippers, a copper (Cu) sacrificial layer was deposited on a silicon (Si) wafer. A pre-stressed bilayer in the shape of the gripper was photo-patterned using photolithography on an ASML stepper mask aligner with 500-nm resolution. E-beam evaporation was used to deposit silicon monoxide (SiO) and silicon dioxide ($SiO_2$). The thicknesses of these layers depended on the desired folding angle and the size of the microgrippers, but ranged from 2 nm to 30 nm thick, including 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, and 30 nm, and fractions thereof. Examples of $SiO/SiO_2$ thickness combinations are given below in Table 1 for several gripper sizes. These thicknesses achieved folding angles between 90° and 115°, including 90°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, and 115°. Subsequently, photolithography was used to define the rigid segment regions which were made of 150 nm to 350 nm of e-beam evaporated SiO. To create the hinge trigger, an outline of the gripper was defined using SPR-220 photoresist to create a mold for the polymer hinge. Warm liquid paraffin was molded on top of the grippers and scraped the excess with a razor blade. The photoresist was dissolved in acetone, which left just the paraffin hinge atop the gripper. The microgrippers were released from the Si wafer using either phosphate buffered saline (PBS) or APS-100 Cu etchant (Transene, Danvers, Mass.).

TABLE 1

Examples of $SiO/SiO_2$ thickness combinations

| Gripper diameter, tip-to-tip (μm) | SiO thickness (nm) | SiO2 thickness (nm) |
| --- | --- | --- |
| 10 | 3 | 3 |
| 35 | 8 | 15 |
| 50 | 9 | 27 |
| 70 | 10 | 30 |

Single Cell Isolation Via an Arrayed Analytical Device:
To fabricate the in vitro arrayed analytical device, microgrippers were fabricated whose base remained attached to the substrate surface after release and folding. The Cu sacrificial layer was initially patterned to expose portions of silicon wafer underneath the base of each gripper. The center of the microgripper was deposited directly onto the silicon wafer, whereas all of the arms were patterned on top of the Cu sacrificial layer. After fabrication as detailed above, almost the entire Cu sacrificial layer was etched from under the gripper arms in APS-100 etchant, leaving a sliver of Cu under the arms to hold them down until the cells were present. A concentrated solution of L929 fibroblasts in culture medium were pipetted on top of the open microgrippers in warm culture media. The cells and microgrippers were left at 37° C. for two to six hours until the microgrippers closed. Untrapped cells were rinsed from the substrate with pipetted L929 culture medium. Captured cells were stained using calcein AM and ethidium homodimer and imaged with fluorescent microscopy and scanning electron microscopy.

Red Blood Cell Capture:

35 µm microgrippers were partially released from the substrate in 1% APS-100 solution for one to three minutes, and rinsed with PBS. Beagle blood diluted in PBS (stained with neutral red dye to enhance their color) (Marshall BioResources) was added to the grippers at 37° C. Grippers closed after one to three hours. Grippers were imaged using optical microscopy.

Film Dissolution:

The dissolution of thin films of SiO and $SiO_2$ in biological solutions was investigated at and above body temperature over a period of 20 days. Using a Filmetrics thickness measurement tool, it was found that SiO degraded at a rate of less than 1 nm/day for the first 10 days, then appeared to plateau (FIG. 3A). It is believed that after these 10 days, the lower limit of the Filmetrics measurement tool was reached. $SiO_2$ cannot be measured by a Filmetrics tool due to surface nonuniformity after dissolution in PBS, so the film dissolution was measured using AFM. It was found that $SiO_2$ degraded at an average rate of 2 nm/day (FIG. 3B), as evidenced by the decreasing hinge thickness. Because the $SiO_2$ is the top layer of the hinge, the 25 nm decrease in film thickness is attributed primarily to $SiO_2$ dissolution in these scans. Optical images taken of 70 µm grippers on Day 0, Day 5, and Day 15 show the $SiO/SiO_2$ hinges of the gripper dissolving (FIG. 3C). The thicker SiO frames remain due to the significantly slower dissolution rate and may completely dissolve after more time.

Effect of Thickness and Time on Thin Film Stress:

The effect of film thickness and time on film stress was investigated for both SiO and $SiO_2$. Using a wafer curvature measurement tool, the stress in varying thicknesses of SiO on a Cu sacrificial layer and varying thicknesses of $SiO_2$ on Cu and SiO layers was calculated. There was significant variation in the stress for each film, due to the large radii of the original Si wafers. Therefore, only data collected on wafers with a radius lower than 700 m was included. There was also significant variation in the stress as a function of time after the films were deposited on the second plot examining the effect of time. $SiO_2$ films became noticeably more tensile when stored over time in air which is possibly due to absorption of water, while SiO remained mostly constant.

Example 2

Fabrication of Grippers

Grippers were fabricated with flexible, pre-stressed bilayer hinges, connected to rigid segments (FIG. 1A). The pre-stressed bilayer was constructed from evaporated thin films of SiO and $SiO_2$. The rigid segments were formed from thicker films of evaporated SiO. An optional hinge trigger made from paraffin could be molded atop the grippers to control actuation. Paraffin remains stiff at room temperature, but begins to melt around 37° C., allowing the grippers to close. These devices can either be arrayed on a substrate for use as a single cell in vitro analytical device or completely released to be used as free-floating tools (FIG. 1B and FIG. 1C).

Figure 2A:
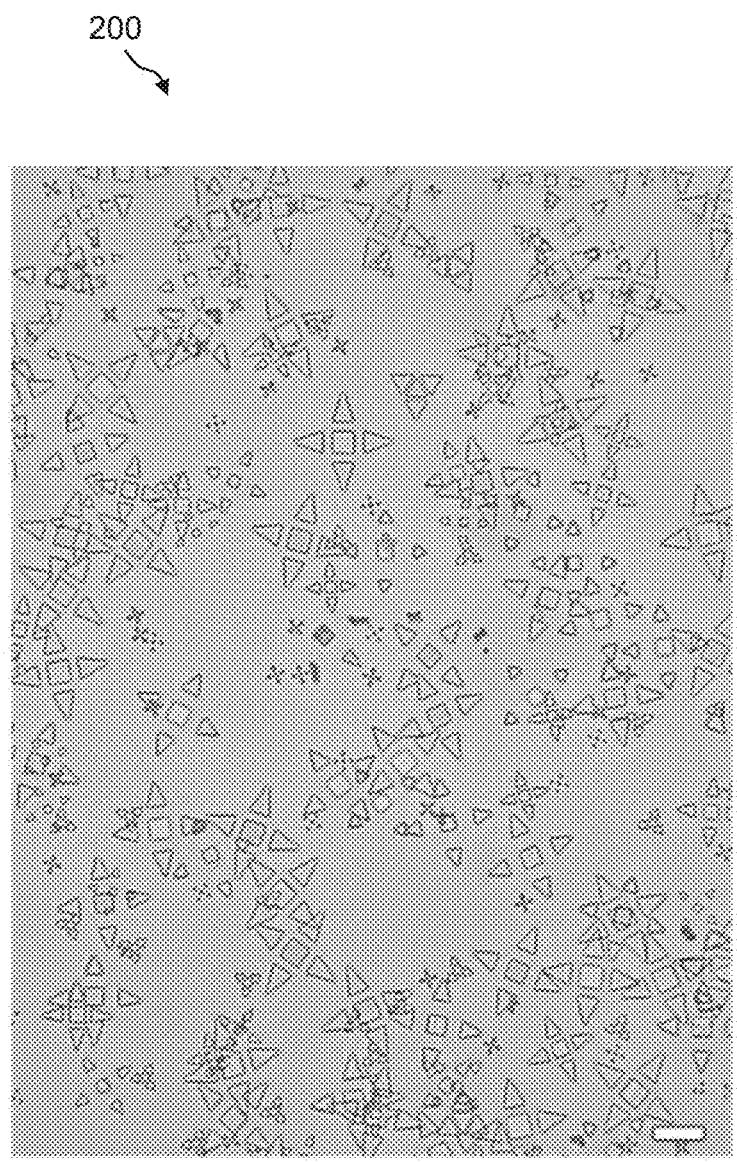
Figure 2B:
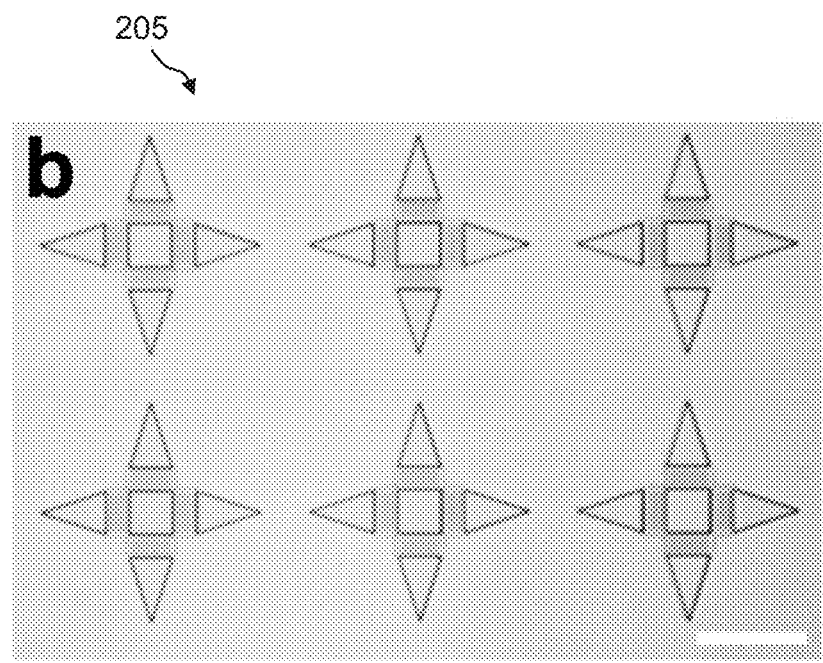
Figure 2C:
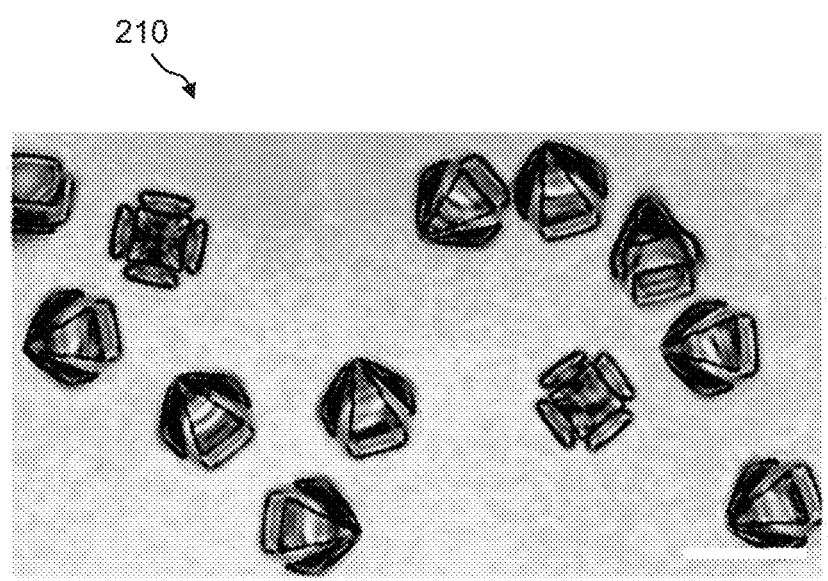
Figure 2D:
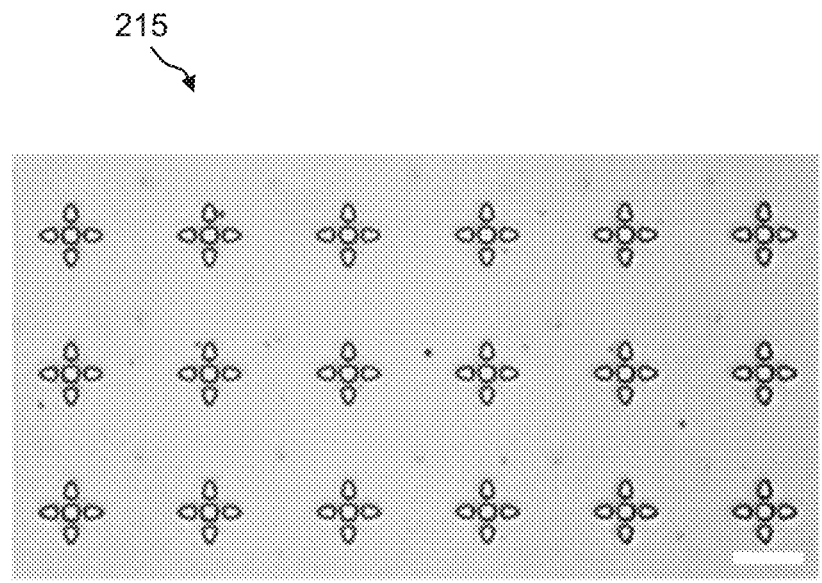
Figure 2E:
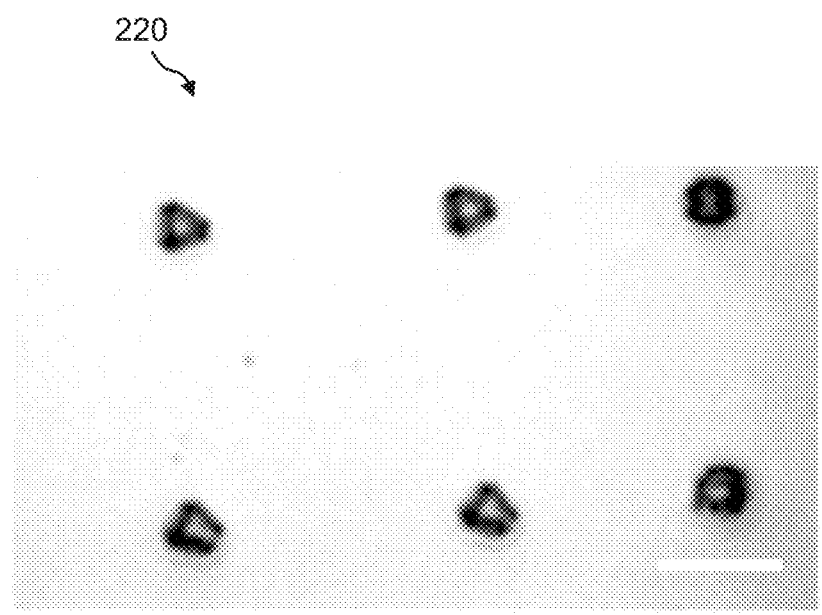
Figure 2F:
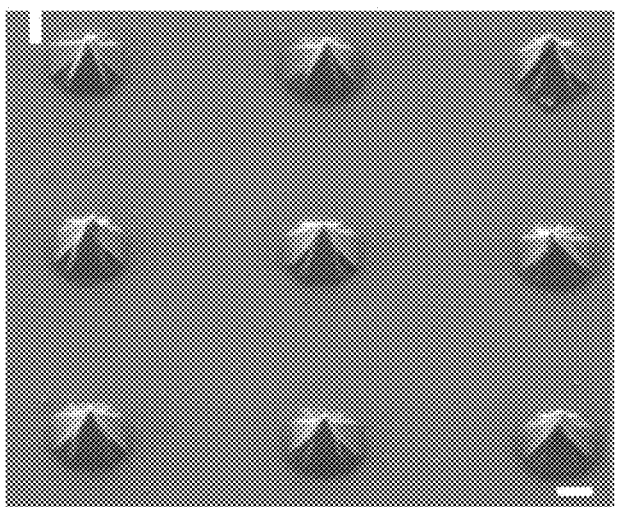
Figure 2G:
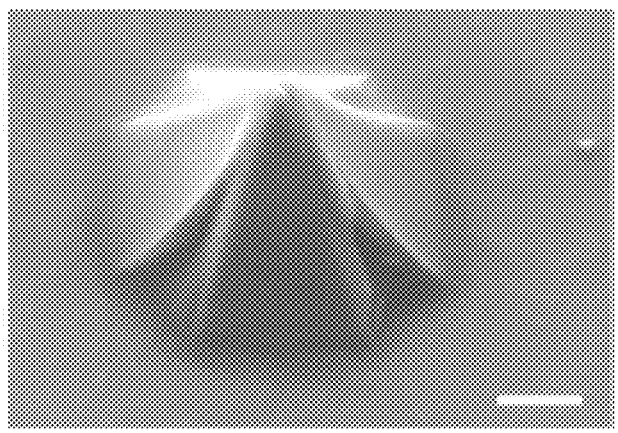

Several designs were created with three or four arms, varying in size from 10 µm to 70 µm in length (tip-to-tip when open) (FIG. 2A). The alternating rigid frames and flexible hinges are evident in the open grippers (FIG. 2B and FIG. 2D). Grippers folded at angles ranging from 90° to 115° depending on the bilayer film thickness, corresponding to folding radii ranging from to 765 nm to 5 µm. The film thickness could be adjusted to create tightly folded grippers in a range of sizes. For example, 9 nm of SiO and 27 nm of $SiO_2$ were deposited to create the 50-µm grippers in FIG. 2B and FIG. 2C, while a bilayer of 3 nm of SiO and 3 nm of $SiO_2$ was used to make the 10-µm grippers in FIG. 2D and FIG. 2E. Despite their small size, these grippers were fabricated using standard photolithography on a projection mask aligner with 500-nm resolution. Photolithography and registry became increasingly difficult as the size of the grippers decreased and 10 µm was the lower limit of well-resolved grippers. Using parallel photolithography instead of serial e-beam lithography afforded rapid, en masse production.

The radius of curvature of the grippers depends directly on the film thickness, mechanical properties of the materials, and residual stress of each layer within the pre-stressed bilayer. It is noteworthy that previous designs of µ-grippers were made from either a chromium/copper (Cr/Cu) bilayer or a chromium/gold (Cr/Au) bilayer (Leong et al., 2009; Gultepe et al., 2012; Gultepe et al., 2013). In these designs, the Cr layer had significant compressive stress (approximately 1 GPa), while the Cu or Au layer was relatively neutral. This stress differential caused the grippers to fold due to the shared boundary between the two layers. These metallic combinations, however, were unable to curl tightly enough to close grippers less than 200 µm in length. The $SiO/SiO_2$ combination, however, provided a sufficiently small radius of curvature for single cell grippers.

Example 3

Characterization of Grippers

The residual stress within each of the SiO and $SiO_2$ layers was characterized. The stress in both SiO and $SiO_2$ was found to be compressive and became more tensile as thicknesses increased from 10 nm to 100 nm (FIG. 4A). These stress values varied significantly with thickness below 100 nm, but were consistent with the expected range of compressive stress for the deposition conditions used (Hill and Hoffman, 1967; Fang et al., 2010). Without wishing to be bound to any one particular theory, it is believed that a more important parameter for film stress is the time of exposure to room air following deposition in an evaporation chamber. It was observed that the absorption of water vapor and room temperature annealing both significantly alter the stress in $SiO_2$ films over time (FIG. 4B). So while the stress in SiO films remained mostly constant over time, the absorption of water by $SiO_2$ caused its tensile stress to grow linearly with the logarithm of aging time, as has been previously reported in the literature (Leplan et al., 1996). By using $SiO_2$ films to form the top of each concave folded hinge, it was ensured that the growth of this tensile stress component helped each hinge fold with a sufficiently small radius of curvature.

In addition, the effect of bending strain and film thickness on folding angle was examined using an analytical curvature model (Nikishkov, 2003) and a computational finite element analysis (FEA) simulation (FIG. 5A, FIG. 5B, FIG. 6A, FIG. 6B, FIG. 6C, FIG. 6D, FIG. 7A, FIG. 7B, FIG. 8A, and FIG. 8B). The effect of strain on bending angle for a 70-µm (FIG. 5A) and a 10-µm gripper (FIG. 5B) was modeled, and it was found that as strain increases, the folding angle also increases which is expected. Folding angle versus SiO and SiO$_2$ film thickness for a 70-μm and a 10-μm gripper also was modeled. These plots can serve as a design guide for determining the necessary thicknesses for each layer within the pre-stressed bilayer to achieve a desired folding angle.

Example 4

Capture of Single Cells by Grippers

To demonstrate an application as an in vitro arrayed analytical tool that could contain single cells for biological experiments, 50-μm grippers were fabricated that remain attached to the substrate upon release. The arms were patterned on the Cu sacrificial layer and thus able to fold. The base of the gripper was patterned directly onto the Si wafer and remained attached during the release and folding process. L-929 fibroblasts in media were pipetted on top of the open grippers. The grippers closed around individual cells after two to six hours in warm culture media due to the slow etching action of the ions in the media (FIG. 9A, FIG. 9B, FIG. 9C, and FIG. 9D). The gripper arms closed tightly around each cell, trapping it within its grasp, but not crushing it as evidenced by an intact cell membrane in a live/dead assay. Some grippers were empty, but when occupied, each of the grippers only contained one cell. The best observed yield for successfully filled grippers was 48% for an area of approximately 75 grippers and the most important factor modulating yield was the concentration of cells used in the suspension. The SiO/SiO$_2$ grippers also are transparent, and thus are ideal for imaging the cells trapped within using optical microscopy techniques. These grippers have slit openings at the intersection of the arms and consequently, nutrients, waste and other biochemicals can flow easily to and from the cells, yet it was observed that the force is strong enough so that the cells do not escape during staining and imaging. A live/dead assay was performed by staining with calcein AM and ethidium homodimer after the cells were captured (FIG. 9A, FIG. 9B, and FIG. 9C). The cells were successfully stained, demonstrating that they are alive, and that the assay chemicals successfully penetrated the grippers. Thus, grippers do not harm the cells, and they allow the cells access to any chemicals within the media.

Figure 9D:
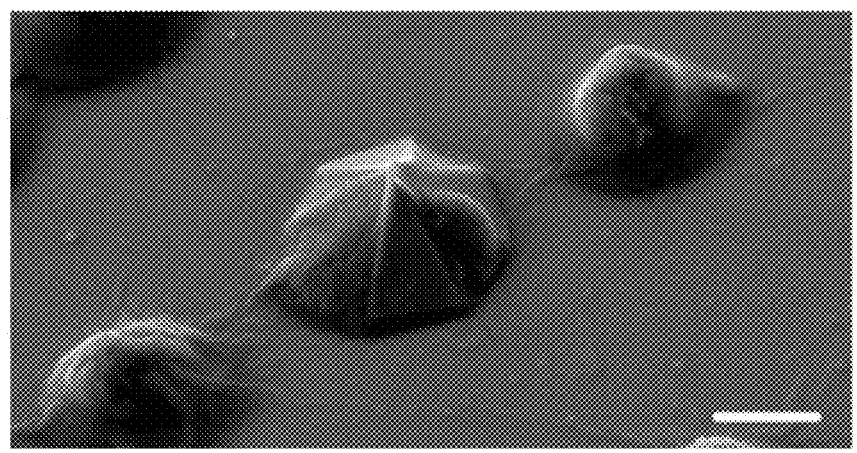

The cells were also fixed and scanning electron microscopy performed on an array of grippers with isolated fixed cells (FIG. 9D). This image confirms that the cell is contained within the arms of the gripper, as opposed to floating on top of the gripper. It is noteworthy that the cells conformed to the shape of the gripper highlighting potential interactions with the faces of the gripper (FIG. 9C and FIG. 9D).

In addition, the applicability of 35-μm grippers to capture red blood cells from a beagle blood sample was investigated (FIG. 10A, FIG. 10B, and FIG. 10C). A 35 μm open gripper size was chosen because it is about 4-5 times the size of the red blood cells (6-8 μm in size). The central palm of these grippers was matched to the size of the red blood cells ensuring that the cells could be entrapped within the gripper in a snug fit. Red blood cells were pipetted onto partially released grippers. Many grippers were able to trap single blood cells within their arms. Optical profilometry and microscopy on the grippers confirmed that the cells were trapped within the grippers. This experiment highlights the potential for these devices as in vivo cell capture tools, with a thermo- or chemo-responsive hinge trigger adapted from previous gripper designs; such devices could easily navigate the intricate conduits of the human body, allowing surgeons to extract single cells in a non-invasive manner from hard-to-reach areas deep within the body. It also is noteworthy that Si and SiO$_2$ (and by extension, SiO, a mixture of Si and SiO$_2$) have been shown to be biodegradable over time when used in dissolvable electronics, making them ideal materials for an in vivo application (Hwang et al., 2012). If needed, such tools could also be created with magnetic elements using highly stressed bilayers of nickel (Ni) with rigid Ni panels for guidance through narrow conduits using magnetic fields (FIG. 11A, FIG. 11B, and FIG. 11C). As an additional form of motion control, patterned biomarkers on the gripper could enable targeting of specific diseased cells in vivo.

In summary, grippers have been designed and fabricated that are capable of capturing and isolating single cells. These single cell grippers, made from biocompatible, optically transparent materials, can be arrayed for high throughput in vitro assays and imaging or released for use as free-floating tools. Varying sizes of these grippers have been employed to capture individual fibroblasts and red blood cells. These cells were alive and could be assayed or fixed for imaging. Because these devices are fabricated in 2D and subsequently folded into 3D, future studies could explore patterned topography such as spikes, holes, and nanoscale roughness, and biochemical surface functionalizations in specific designs onto one or more device walls. This approach could enable multiple assays to be run at one time on a single cell. Additionally, previous studies have demonstrated the fabrication of many different shaped of polyhedral (Leong et al., 2008; Pandey et al., 2011). Future studies could utilize these pyramidal grippers and other regular polyhedra to study the effect of 3D confinement on cell growth and morphology. Additionally, the presently disclosed process is amenable to other lithographic approaches such as e-beam or nanoimprint lithography for sub-cellular gripping capabilities. Finally, the presently disclosed subject matter highlights the potential for these tools as in vivo cell capture tools, capable of navigating intricate conduits within the circulatory, central nervous, and urinogenital systems.

Example 5

Gripper Folding Model

The folding of gripper is simulated in finite element analysis software Abaqus. This model simulates the complete process of gripper folding triggered by pre-load initial strain. The gripper is simplified as a thin bilayer, composed of one fixed palm, a deformable hinge, and a stiff panel.

Dimensions:

Dimensions of 10-μm and 70-μm grippers are obtained from AutoCAD file.

Material Properties:

The layers are made of elastic isotropic material with following properties. Mechanical properties for SiO$_2$ are well defined in the literature (Halg, 1990; Kim, 1996) but properties for SiO are less commonly reported. Hence, mechanical properties of SiO were assumed to be between that of amorphous Si (Freund and Suresh, 2003) and SiO$_2$, given that SiO is a two-phase, non-homogenous mixture of amorphous Si and SiO$_2$ with some chemical bonding occurring at the interface of the phases (Friede and Jansen, 1996; Schulmeister and Mader, 2003). The initial stress was taken from measurements detailed above in the Effect of thickness and time on thin film stress section (Materials and Methods). The properties used are listed in Table 2.

TABLE 2

Bilayer thin film properties used in the FEA model

| Property | SiO | SiO$_2$ |
| --- | --- | --- |
| Young's Modulus (E, in GPa) | 77 | 75 |
| Poisson Ratio (υ) | 0.2 | 0.17 |
| Initial stress (σ, in MPa) | −344 | −2 |

Section:

The bilayer is considered as a composite shell due to large aspect ratio between length and thickness (about 1000:1). Each layer is assigned with designed thickness, with 3 integration points in Simpson integration rule. Further incrementing of integration points to 9 does not affect final results.

TABLE 3

Gripper dimensions used in finite element simulation.

| | 10 μm Gripper | 70 μm Gripper |
| --- | --- | --- |
| SiO Thickness/nm | 3 | 10 |
| SiO$_2$ Thickness/nm | 3 | 30 |
| Hinge Length/μm | 1.35 | 9.55 |
| Hinge Width/μm | 1.80 | 12.70 |

Boundary Condition:

Deformation is only applied to the hinge. One end of the hinge is fixed in all three directions while the other is free to bend with a fixed length. Displacement of the palm (middle part of gripper) is zero in all x, y, and z directions, representing the fixed boundary of the hinge. The initial strain determines final folding angle. In Abaqus, the initial strain is simulated by assigning the two materials in bilayer with different thermal expansion coefficients, and applying temperature field only to the hinge region to realize the initial strain differential.

$$\Delta \varepsilon = \Delta \alpha \cdot \Delta T = \frac{\sigma_1}{E_1} - \frac{\sigma_2}{E_2}$$

where the stresses and mechanical properties of each film are given above in Table 2.

For FIG. 5A and FIG. 5B, the effects of preload strain on folding angle (with fixed thickness from Table 3) were examined. To create this graph, the preload strain from zero to the maximum value when the gripper completely folds was varied. For effect of thickness on folding angle, also shown in FIG. 5A and FIG. 5B, the preload strain as 0.0043 based on the film properties given in Table 2 was fixed and each layer thickness was varied as noted in the graph.

Mesh and Step:

The center and each hinge are meshed with 20×20 structured elements, and the nondeformable panel is meshed with 10×10 structured elements. Further incrementing of mesh numbers to 30×30 do not change the results. Large deformation is expected. Therefore, nonlinear effects of large deformation and displacement are considered during strain ramp from zero to the measured value.

TABLE 4

Comparison of experimentally-observed and analytically predicted folding angles

| Gripper diameter (μm) | SiO/SiO$_2$ thickness (nm) | Hinge gap (μm) | Analytical model predicted folding angle | FEA model predicted folding angle | Observed folding angle |
| --- | --- | --- | --- | --- | --- |
| 70 | 10/30 | 9.55 | 82° | 87° | 110° |
| 10 | 3/3 | 1.35 | 103° | 105° | 101° |

Comparison of Folding Angle Between Experiment, Analytical Model, and FEM Simulation:

The experimentally observed folding angle to the folding angles predicted by both the analytical curvature model and the FEA simulation was compared, as shown in FIG. 6A, FIG. 6B, FIG. 6C, and FIG. 6D and Table 4. These results demonstrate agreement between the analytical model and the computational simulation, and are within 20% of what we observed experimentally, which is a reasonable level of agreement for design purposes. Any differences were attributed mainly to errors in the measured values of evaporated film thickness and stress.

Example 6

Effects of Film Thickness on Bending

A sensitivity analysis was performed to investigate the variation of fold angle with strain and thickness. The effects of thickness were analyzed with the same thin film curvature analytical model used in Example 5 above (Nikishkov, 2003; Schulmeister and Mader, 2003).

For a bilayer of two thin films the material properties and film thicknesses can be used to calculate the curvature, K.

For a double layer, $$K = \frac{6E'_1 E'_2 t_1 t_2 (t_1 + t_2)(\eta_1 \varepsilon_1^0 - \eta_2 \varepsilon_2^0)}{(E'_1)^2 t_1^4 + (E'_2)^2 t_2^4 + 2E'_1 E'_2 t_1 t_2 (2t_1^2 + 2t_2^2 + |3t_1 t_2)}$$

The folding angle is calculated using, $\alpha = l \cdot K \cdot 180 \, \pi$. For this case, with the plane strain condition, $E_i' = E_i/(1-v_i^2)$, $\eta_i = 1 + v_i$, $\varepsilon_i^0 = \sigma_j^0/E_i$ (E, Young's modulus; v, Poisson's Ratio; t, thickness; $\sigma^0$, initial stress; $\varepsilon^0$, initial strain; l, hinge length). In these calculations, values listed in Tables 2 and 3 were used.

For this analysis, stress is considered to be constant with film thickness since the variation in thickness is slight for each material. For a 70-μm gripper, as SiO thickness increases, the folding angle increases slightly; as SiO$_2$ thickness decreases, the folding angle decreases considerably (FIG. 7A and FIG. 7B). For a 10-μm gripper, the folding angle decreases with the increase of film thickness (FIG. 8A and FIG. 8B). Therefore, in 10-μm and 70-μm gripper, the film thickness is also a factor which affects the final folding angle. The graphs shown in FIG. 7A, FIG. 7B, FIG. 8A, and FIG. 8B, along with the graphs in FIG. 5A and FIG. 5B, provide design suggestions for others wishing to create similar grippers for a range of desired folding angles.

Example 7

Magnetic Ni/Ni Single Cell Grippers

The use of ion beam assisted deposition (IBAD) significantly alters the stress in thin films as compared to e-beam deposition without ion beam assistance. For example, the stress in nickel films evaporated using traditional e-beam evaporation is on the order of 500 MPa tensile, whereas the stress in nickel films deposited with IBAD is approximately −300 MPa compressive. This differential in stress can be utilized to achieve tightly curling films such as the ones described herein with SiO and $SiO_2$. These Ni/Ni single cell grippers were investigated with paraffin hinge triggers as free-floating single cell capture tools that could be controlled via a magnetic field and thermally actuated at body temperature. FIG. 11A, FIG. 11B, and FIG. 11C depict 70-μm Ni/Ni grippers open with a paraffin hinge trigger and tightly closed after release from the substrate.

Example 8

Capturing and Manipulating Single Cells in 3D with Thermo-Responsive Microgrippers Introduction:

Presently, tissue biopsies and cell cultures utilize many cells to get a statistical representation of a given environment. The ability to retrieve and manipulate single cells, however, allows for a closer examination of individual cell behavior and characteristics. While single cell work is a growing field, the method of retrieval and manipulation of single cells is often difficult, time consuming, and requires large devices or equipment. Large microgrippers have previously been utilized (500 μm in diameter) for gastrointestinal biopsies (Gultepe, 2013). Herein, tetherless microgrippers have been demonstrated ranging in size from 10 μm to 50 μm that can capture and manipulate individual cells. These devices can be used in vivo as thermo-responsive tools for single cell biopsies or in vitro as single cell isolation chambers for studying the effects of micropatterned biochemicals and topography on internal cell development and cell division.

Materials and Methods:

Microgrippers were designed with pre-stressed bilayer hinges connected to rigid segments with folding controlled by a thermo-responsive trigger layer atop the hinges. Initially, a chromium (Cr) and copper (Cu) sacrificial layer was deposited on a silicon wafer. Then the flexible hinges were micropatterned, using either a silicon monoxide (SiO) and silicon dioxide bilayer or a double nickel (Ni) bilayer, where the two layers have different intrinsic stresses. Subsequently, SiO or Ni rigid segments were patterned atop the flexible hinges. Finally, polyvinyl alcohol (PVA) was micromolded as the thermoresponsive trigger layer, which could easily dissolve in 37° C. aqueous solutions. Microgrippers were released by etching the Cu layer in PBS. Cell manipulation and isolation experiments were performed with murine L-929 fibroblasts stained with calcein AM.

Figure 12A:
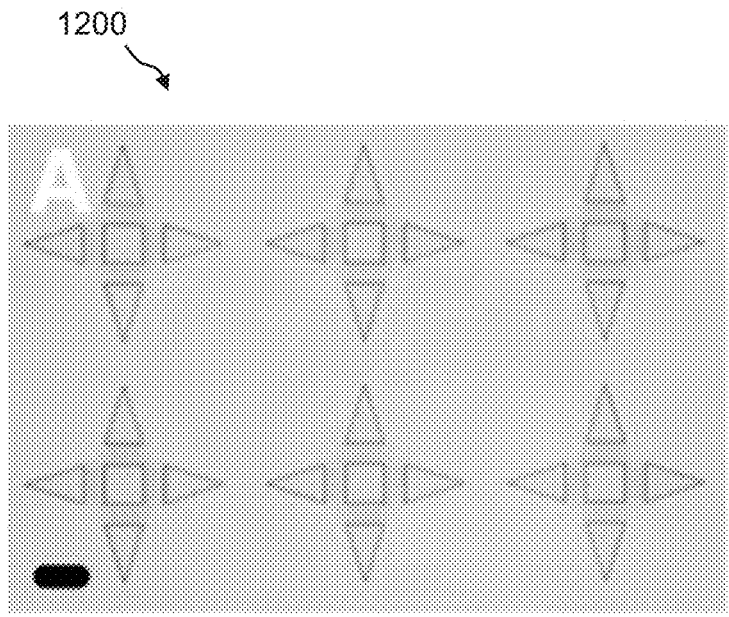
Figure 12B:
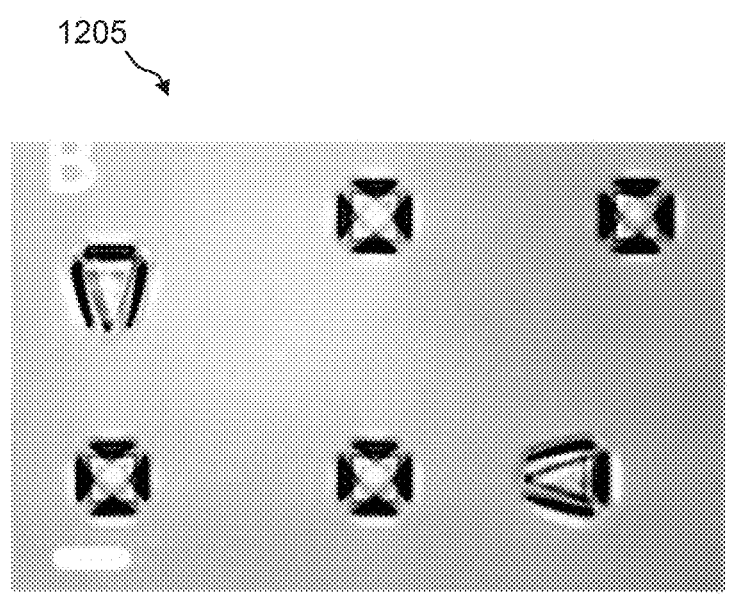
Figure 12C:
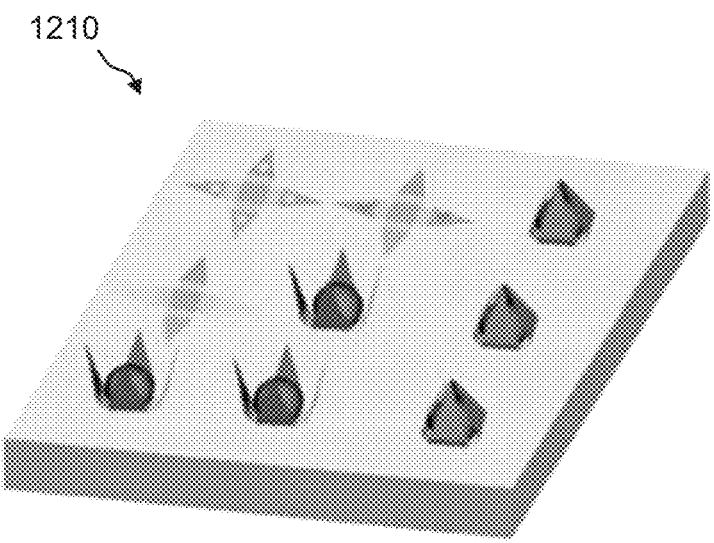
Figure 12D:
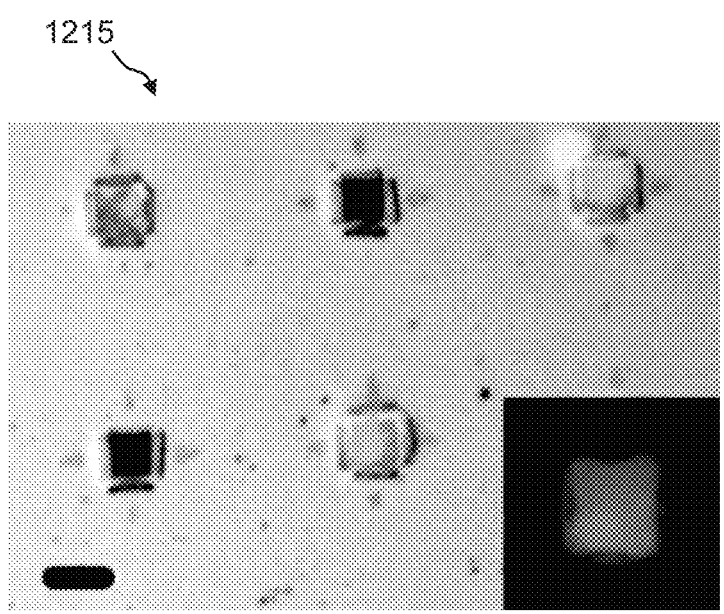

Results and Discussion:

Microgrippers were used in vitro to isolate and study single cell structure in response to micropatterned biochemicals and topography in 3D (FIG. 12A and FIG. 12B). Microgrippers were designed to remain attached to a silicon wafer, with arms free to capture cells (FIG. 12C). Cells captured within the microgrippers conformed to the shape of the microgripper, in this case (but not limited to) a pyramid with a square base (FIG. 12D). The internal structure of cells can be affected by patterning gold and fibronectin selectively on a few arms or portions of an arm (FIG. 12C), so that portions of each arm attract cells and other portions repel cells. In this way, the effect of micropatterned biochemicals on individual cells can be studied in 3D. Holes or very thick features can also be patterned on the gripper arms to study the effects of topography on internal cell organization. Potential in vivo cell biopsy applications were also demonstrated using 50-μm Ni microgrippers which close after 10 minutes at body temperature to capture and move individual stained cells in a capillary tube from afar using a magnet.

Conclusions:

Microgrippers were used to capture, isolate, and manipulate single cells for in vitro biomedical applications and for potential for in vivo applications. The way that 3D topography and micropatterned cell-attractive and -repellent biochemicals influence internal, individualized cell arrangement and cell division was studied. These microgrippers can also be utilized to magnetically capture and move cells, demonstrating promise for in vivo cell biopsies, for applications such as blood cancer biopsies.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Alexander A. Solovev; Yongfeng Mei; Esteban Bermúdez Ureña; Gaoshan Huang; Schmidt, O. G. *Small* 2009, 5(14): 1688-1692.

Altschuler, S. J.; Wu, L. F. *Cell* 2010, 141:559-563.

Arora, W. J.; Nichol, A. J.; Smith, H. I.; Barbastathis, G. *Applied Physics Letters* 2006, 88, 053108.

Ashkin, A.; Dziedzic, J. M.; Bjorkholm, J. E.; Chu, S. *Optics Letters* 1986, 11: 288-290.

Azioune, A.; Storch, M.; Bornens, M.; Thery, M.; Piel, M. *Lab on a Chip* 2009, 9:1640-1642.

Bassik, N.; Stern, G. M.; Jamal, M.; Gracias, D. H. *Advanced Materials* 2008, 20(24): 4760-4764.

Bassik, N.; Stern, G. M.; Gracias, D. H. *Applied Physics Letters* 2009, 95: 091901.

Bassik, N.; Brafman, A.; Zarafshar, A. M.; Jamal, M.; Luvsanjav, D.; Selaru, F. M.; Gracias, D. H. *Journal of the American Chemical Society* 2010, 132 (46):16314-16317.

Beckman, R. A.; Schemmann, G. S.; Yeang, C.-H. *Proceedings of the National Academy of Sciences* 2012, 109(36): 14586-14591.

Berns, M. W.; Tadir, Y.; Liang, H.; Tromberg, B. *Methods Cell Biol.* 1998, 55:71-98.

Calbo, J.; van Montfort, E.; Proost, N.; van Drunen, E.; Beverloo, H. B.; Meuwissen, R.; Berns, A. *Cancer Cell* 2011, 19, 244-256.

Chalapat, K.; Chekurov, N.; Jiang, H.; Li, J.; Parviz, B.; Paraoanu, G. S. *Advanced Materials* 2013, 25(1): 1.

Charnley, M.; Textor, M.; Khademhosseini, A.; Lutolf, M. *Integrative biology* 2009, 1, 625-634.

Chronis, N.; Lee., L. P. *Journal of Microelectromechanical Systems* 2005, 14 (4): 857-863.

Chua, C. L.; Fork, D. K.; van Schuylenbergh, K.; Lu, J.-P. *Journal of Microelectromechanical Systems* 2003, 12 (6): 989-995.

Di Carlo, D.; Aghdam, N.; Lee, L. *Analytical Chemistry* 2006, 78:4925-4930.

Di Carlo, D.; Tse, H. T. K.; Gossett, D. R. Introduction: Why Analyze Single Cells? In *Single-Cell Analysis: Methods and Protocols*, Lindstrom, S.; Andersson-Svahn, H., Eds. Springer Science+Business Media: 2012; Vol. 853.

Di Carlo, D.; Wu, L. Y.; Lee, L. *Lab on a Chip* 2006, 6, 1445-1449.

Ding, X.; Lin, S.-C. S.; Kiraly, B.; Yue, H.; Li, S.; Chiang, I.-K.; Shi, J.; Benkovic, S. J.; Huang, T. J. *Proceedings of the National Academy of Sciences* 2012, 109 (28): 11105-11109.

Fang, M.; Hu, D.; Shao, J. *Chinese Optics Letters* 2010, 8(1): 119-122.

Fernandes, R.; Gracias, D. H. *Materials Today* 2009, 12(10): 14-20.

Freund, L. B.; Suresh, S., *Thin Film Materials*. Cambridge University Press: 2003.

Friede, B.; Jansen, M. *Journal of Non-Crystalline Solids* 1996, 204: 202-203.

Gautrot, J. E.; Trappmann, B.; Oceguera-Yanez, F.; Connelly, J.; He, X.; Watt, F. M.; Huck, W. T. S. *Biomaterials* 2010, 31(18): 5030-5041.

Gultepe, E.; Randhawa, J. S.; Kadam, S.; Yamanaka, S.; Selaru, F. M.; Shin, E. J.; Kalloo, A. N.; Gracias, D. H. *Advanced Materials* 2012.

Gultepe, E.; Yamanaka, S.; Laflin, K. E.; Kadam, S.; Shim, Y.; Olaru, A. V.; Limketkai, B.; Khashab, M. A.; Kalloo, A. N.; Gracias, D. H.; Selaru, F. M. *Gastroenterology* 2013, 144 (4): 691-693.

Halg, B. In On a non-volatile memory cell based on micro-electro-mechanics, IEEE Micro Electro Mechanical Systems Workshop, Napa Valley, Calif., 1990; pp 174-175.

Harazim, S. M.; Xi, W.; Schmidt, C. K.; Sanchez, S.; Schmidt, O. G. *Journal of Materials Chemistry* 2012, 22(7): 2878-2884.

Hill, A. E.; Hoffman, G. R. *British Journal of Applied Physics* 1967, 18(1): 13.

Huang, M.; Boone, C.; Roberts, M.; Savage, D. E.; Lagally, M. G.; Shaji, N.; Qin, H.; Naim, J. A.; Liu, F. *Advanced Materials* 2005, 17(23):2860-2864.

Huang, G.; Mei, Y.; Thurmer, D. J.; Coric, E.; Schmidt, O. G. *Lab on a Chip* 2009, 9: 263-268.

Hwang, S.-W.; Tao, H.; Kim, D.-H.; Cheng, H.; Song, J.-K.; Rill, E.; Brenckle, M. A.; Panilaitis, B.; Won, S. M.; Kim, Y.-S.; Song, Y. M.; Yu, K. J.; Ameen, A.; Li, R.; Su, Y.; Yang, M.; Kaplan, D. L.; Zakin, M. R.; Slepian, M. J.; Huang, Y.; Omenetto, F. G.; Rogers, J. A. *Science* 2012, 337(6102): 1640-1644.

Iler, R. K. *Journal of Colloid and Interface Science* 1973, 43(2): 399-408.

Kane, R. S.; Takayama, S.; Ostuni, E.; Ingber, D. E.; Whitesides, G. M. *Biomaterials* 1999, 20:2363-2376.

Kazuyoshi, K.; Fleischmann, T.; Saravanan, S.; Vaccaro, P. O.; Aida, T. *Japanese Journal of Applied Physics* 2003, 42, 4079-4083.

Kim, M. T. *Thin Solid Films* 1996, 283(1-2): 12-16.

Kim, S.; Qiu, F.; Kim, S.; Ghanbari, A.; Moon, C.; Zhang, L.; Nelson, B.; Choi, H. *Advanced Materials* 2013, 25(41): 5863-5868.

Leclair, A. M.; Ferguson, S. S. G.; Lagugne-Labathet, F. *Biomaterials* 2011, 32(5):1351-1360.

Leong, T. G.; Benson, B. R.; Call, E. K.; Gracias, D. H. *Small* 2008, 4(10): 1605-1609.

Leong, T. G.; Randall, C. L.; Benson, B. R.; Bassik, N.; Stern, G. M.; Gracias, D. H. *Proceedings of the National Academy of Sciences* 2009, 106 (3): 703-708.

Leplan, H.; Robic, J. Y.; Pauleau, Y. *Journal of Applied Physics* 1996, 79(9):6926-6931.

Lindstrom, S.; Andersson-Svahn, H. *Lab on a Chip* 2010, 10: 3363-3372.

Lindstrom, S.; Andersson-Svahn, H. *Biochimica et Biophysica Acta* 2011, 1810 (3): 308-316.

Lindstrom, S.; Andersson-Svahn, H. *Single Cell Analysis: Methods and Protocols*. Springer Science+Business Media: New York, 2012; Vol. 853.

Lúcio, A.; Santos, R.; Mesquita, O. *Physical Review E* 2003, 68: 041906.

Ma, C.; Fan, R.; Admad, H.; Shi, Q.; Comin-Anduix, B.; Chodon, T.; Koya, R. C.; Liu, C.-C.; Kwong, G. A.; Radu, C. G.; Ribas, A.; Heath, J. R. *Nature Medicine* 2011, 17 (6):738-743.

Mandal, K.; Balland, M.; Bureau, L. *PLoS ONE* 2012, 7(5): e37548.

Mannello, F. *BioMed Central Medicine* 2013, 11: 169-173.

Mei, Y.; Huang, G.; Solovev, A. A.; Bermudez Urena, E.; Monch, I.; Ding, F.; Reindl, T.; Fu, R. K. Y.; Chu, P. K.; Schmidt, O. G. *Advanced Materials* 2008, 20(21): 4085-4090.

Mei, Y.; Thurmer, D. J.; Deneke, C.; Kiravittaya, S.; Chen, Y.-F.; Dadgar, A.; Bertram, F.; Bastek, B.; Krost, A.; Christen, J.; Reindl, T.; Stoffel, M.; Coric, E.; Schmidt, O. G. *ACS Nano* 2009, 3(7): 1663-1668.

Moiseeva, E.; Senousy, Y. M.; Harnett, C. K. *Journal of Micromechanics and Microengineering* 2007, 17(9): N63-N68.

Navin, N.; Krasnitz, A.; Rodgers, L.; Cook, K.; Meth, J.; Kendall, J.; Riggs, M.; Eberling, Y.; Troge, J.; Grubor, V.; Levy, D.; Lundin, P.; Maner, S.; Zetterberg, A.; Hicks, J.; Wigler, M. *Genome Research* 2010, 20:68-80.

Nikishkov, G. P. *Journal of Applied Physics* 2003, 94:5333-5336.

Nilsson, J.; Evander, M.; Hammarström, B.; Laurell, T. *Analytica Chimica Acta* 2009, 649 (2):141-157.

Pandey, S.; Ewing, M.; Kunas, A.; Nguyen, N.; Gracias, D. H.; Menon, G. *Proceedings of the National Academy of Sciences* 2011, 108(50): 19885-19890.

Park, S.; Zhang, Y.; Wang, T. H.; Yang, S. *Lab on a Chip* 2011, 11: 2893-2900.

Peng, X.; Li, P. *Analytical Chemistry* 2004, 76:5273-5281.

Peng, X.; Li, P. *Analytical Chemistry* 2004, 76:5282-5292.

Pietras, A. *Advances in Cancer Research* 2011, 112: 255-281.

Prinz, V. Y.; V. A Seleznev; A. K Gutakovsky; A. V Chehovskiy; V. V Preobrazhenskii; M. A Putyato; Gavrilova, T. A. *Physica E: Low-dimensional Systems and Nanostructures* 2000, 6(1-4): 828-831.

Prinz, V. Y. *Russian Physics Journal* 2003, 46(6): 568-576.

Rimstidt, J. D.; Barnes, H. L. *Geochimica et Cosmochimica Acta* 1980, 44 (11): 1683-1699.

Roman, G. T.; Chen, Y.; Viberg, P.; Culbertson, A. H.; Culbertson, C. T. *Analytical and Bioanalytical Chemistry* 2007, 387 (1): 9-12.

Sakar, M. S.; Steager, E. B.; Kim, D. H.; Kim, M. J.; Pappas, G. J.; Kumar, V. *Applied Physics Letters* 2010, 96:043705.

Sasaki, M.; Briand, D.; Noell, W.; de Rooij, N. F. *IEEE Journal of Selected Topics in Quantum Electronics* 2004, 10(3): 455-461.

Schmidt, O. G.; Eberl, K. *Nature* 2001, 410:168.

Schulmeister, K.; Mader, W. *Journal of Non-Crystalline Solids* 2003, 320:143-150.

Shenoy, V. B.; Gracias, D. H. *MRS Bulletin* 2012, 37, (9), 847-854.

Smith, E. J.; Xi, W.; Makarov, D.; Mönch, I.; Harazim, S.; Bolanos Quiñones, V. A. B.; Schmidt, C. K.; Mei, Y.; Sanchez, S.; Schmidt, O. G. *Lab on a Chip* 2012, 12 (11): 1917-1931.

Soler, L.; Magdanz, V.; Fomin, V. M.; Sanchez, S.; Schmidt, O. G. *ACS Nano* 2013, 7(11): 9611-9620.

Stellman, P.; Buchner, T.; Arora, W. J.; Barbastathis, G. *Journal of Microelectromechanical Systems* 2007, 16(4): 932-949.

Townes-Anderson, E.; St Jules, R. S.; Sherry, D.; Lichtenberger, J.; Hassanain, M. *Molecular Vision* 1998, 4:12.

Valero, A.; Merino, F.; Wolbers, F.; Luttge, R.; Vermes, I.; Andersson, H.; van den Berg, A. *Lab on a Chip* 2005, 5, 49-55.

Wheeler, A. R.; Throndset, W. R.; Whelan, R. J.; Leach, A. M.; Zare, R. N.; Liao, Y. H.; Farrell, K.; Manger, I. D.; Daridon, A. *Analytical Chemistry* 2003, 75: 3581-3586.

Xi, W.; Solovev, A. A.; Ananth, A. N.; Gracias, D. H.; Sanchez, S.; Schmidt, O. G. *Nanoscale* 2012, 5:1294-1297.

Xie, C.; Dinno, M. A.; Li, Y.-q. *Optics Letters* 2002, 27 (4):249-251.

Zhang, H.; Liu, K.-K. *Journal of The Royal Society Interface* 2008, 5:671-690.

Zhanga, L.; Goloda, S. V.; Deckardta, E.; Prinz, V. Y.; Grützmachera, D. *Physica E: Low-dimensional Systems and Nanostructures* 2004, 23(3-4): 280-284.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A device for sampling one or more single cells in a tissue sample or biological fluid, the device comprising: a hinge comprising a pre-stressed bilayer, wherein the hinge has a folding angle ranging from about 90 degrees to about 115 degrees and wherein the hinge is in operational communication with one or more rigid segments, wherein the one or more rigid segments comprise a plurality of arms having sharp or tapered tips, wherein the device has a first configuration capable of being actuated to at least a second configuration in response to one or more stimuli, and wherein the device is adapted to capture, manipulate, or encapsulate the one or more single cells from the tissue sample or biological fluid when in the second configuration; wherein the device has a dimension having a range from about 10 µm to about 70 µm measured from at least one tip of the plurality of arms to at least one other tip of the plurality of arms, wherein the device is optically transparent and bioresorbable.

2. The device of claim 1, wherein the pre-stressed bilayer comprises $SiO/SiO_2$.

3. The device of claim 1, wherein the one or more rigid segments comprise SiO.

4. The device of claim 1, wherein the one or more rigid segments comprise Ni.

5. The device of claim 1, wherein the device has a shape selected from a star and a sphere, wherein each shape comprises the plurality of arms having sharp or tapered tips.

6. The device of claim 1, wherein the plurality of arms further comprise one or more materials that either attract or repel the cell and combinations thereof.

7. The device of claim 6, wherein the one or more materials are selected from gold and fibronectin.

8. The device of claim 1, wherein the plurality of arms are patterned with one or more features selected from one or more holes and one or more raised topographical structures.

9. The device of claim 1, further comprising one or more openings or slits at an intersection of at least two arms, wherein the one or more openings or slits are in fluid communication with the one or more single cells captured by the device such that nutrients, waste, and physiological biochemical can flow to and from the one or more single cells.

10. The device of claim 1, wherein the device is adapted to be deployed in a subject.

11. The device of claim 10, wherein the device is adapted to be deployed in the subject by an apparatus selected from a capsule, a sustained-release capsule, an endoscope, a laparoscope, and a suppository or a method selected from an enema and an injection.

12. The device of claim 1, wherein the one or more stimuli is selected from a change in temperature, a change in pH, an acid, a biochemical, an enzyme, a soluble protein, and a surface biomarker.

13. An array comprising a plurality of devices of claim 1, wherein the plurality of devices can optionally include one or more unique biomolecular markers, optical patterns, and electronic patterns, and combinations thereof.

14. A method for sampling a single cell in a tissue sample or biological fluid of a subject, the method comprising:
(a) introducing to the subject a plurality of sampling devices comprising: a hinge comprising a pre-stressed bilayer, wherein the hinge has a folding angle ranging from about 90 degrees to about 115 degrees and wherein the hinge is in operational communication with one or more rigid segments, wherein the one or more rigid segments comprise a plurality of arms having sharp or tapered tips, wherein the plurality of sampling devices have a first configuration capable of being actuated to at least a second configuration in response to one or more stimuli, and wherein the plurality of sampling devices are adapted to capture, manipulate, or encapsulate the single cell from the tissue sample or biological fluid when in a second configuration; wherein the plurality of sampling devices have a dimension having a range from about 10 µm to about 70 µm measured from at least one tip of the plurality of arms to at least one other tip of the plurality of arms, wherein the plurality of sampling devices are optically transparent and bioresorbable;
(b) contacting the plurality of sampling devices with a tissue site or biological fluid;
(c) altering a configuration of the plurality of sampling devices from the first configuration to the second configuration while in contact with the tissue site or biological fluid, the second configuration adapted such that the plurality of sampling devices grasps the tissue sample or samples the biological fluid at a discrete location; and
(d) releasing and/or collecting the plurality of sampling devices.

15. The method of claim 14, further comprising inserting the plurality of sampling devices into a capsule before introducing the plurality of sampling devices to the subject.

16. The method of claim 14, wherein the plurality of sampling devices comprises between about 2 to about 10,000 sampling devices.

17. The method of claim 14, wherein the one or more stimuli is selected from the group consisting of a change in temperature, a change in pH, an acid, a biochemical, an enzyme, a soluble protein, and a surface biomarker.

18. The method of claim 17, wherein the change in temperature comprises changing the temperature above about body temperature.

19. The method of claim 18, wherein the change in temperature comprises changing the temperature above about 32° C.

20. The method of claim 14, wherein the tissue site is selected from the group consisting of the esophagus, stomach, duodenum, small intestine, large intestine, the circulatory system, the respiratory system, the urinogenital system, central nervous system.

21. The method of claim 14, wherein the tissue site comprises diseased tissue.

22. The method of claim 21, wherein the diseased tissue is selected from the group consisting of a tumor, a fistula, and an abscess.

23. The method of claim 14, wherein sampling the single cell in the tissue sample or biological fluid of the subject comprises diagnosing the subject for a disease, condition, disorder, or symptom.

24. The method of claim 23, wherein the disease, condition, disorder, or symptom is a disease, condition, disorder, or symptom of the gastrointestinal (GI) tract, the circulatory system, the respiratory system, the urinogenital system, central nervous system.

25. The method of claim 23, wherein the disease, condition, disorder, or symptom comprises a cancer.

* * * * *